US010682314B2

(12) United States Patent
Gourapura et al.

(10) Patent No.: US 10,682,314 B2
(45) Date of Patent: Jun. 16, 2020

(54) NANOPARTICLE BASED VACCINE STRATEGY AGAINST SWINE INFLUENZA VIRUS

(71) Applicant: OHIO STATE INNOVATION FOUNDATION, Columbus, OH (US)

(72) Inventors: Renukaradhya Gourapura, Wooster, OH (US); Santosh Dhakal, Wooster, OH (US); Jagadish Hiremath, Wooster, OH (US); Chang-Won Lee, Wooster, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/575,734

(22) PCT Filed: May 26, 2016

(86) PCT No.: PCT/US2016/034316

§ 371 (c)(1),
(2) Date: Nov. 20, 2017

(87) PCT Pub. No.: WO2016/191553

PCT Pub. Date: Dec. 1, 2016

(65) Prior Publication Data

US 2018/0243228 A1 Aug. 30, 2018

Related U.S. Application Data

(60) Provisional application No. 62/166,344, filed on May 26, 2015.

(51) Int. Cl.

| | |
|---|---|
| *A61K 39/00* | (2006.01) |
| *A61K 39/12* | (2006.01) |
| *C07K 14/005* | (2006.01) |
| *A61K 48/00* | (2006.01) |
| *A61K 9/127* | (2006.01) |
| *A61K 9/51* | (2006.01) |
| *C12N 7/06* | (2006.01) |
| *A61P 31/16* | (2006.01) |
| *A61K 39/145* | (2006.01) |
| *C12N 7/00* | (2006.01) |

(52) U.S. Cl.
CPC ............ *A61K 9/5153* (2013.01); *A61K 39/12* (2013.01); *A61K 39/145* (2013.01); *A61P 31/16* (2018.01); *C12N 7/00* (2013.01); *C12N 7/06* (2013.01); *A61K 2039/5252* (2013.01); *A61K 2039/543* (2013.01); *A61K 2039/544* (2013.01); *A61K 2039/552* (2013.01); *A61K 2039/55555* (2013.01); *A61K 2039/57* (2013.01); *C12N 2760/16134* (2013.01); *C12N 2760/16161* (2013.01)

(58) Field of Classification Search
CPC .. A61K 39/12; A61K 38/193; A61K 2300/00; A61K 31/7115; C07K 14/005
See application file for complete search history.

(56) References Cited

U.S. PATENT DOCUMENTS

| | | | | |
|---|---|---|---|---|
| 4,436,727 | A | 3/1984 | Ribi | |
| 4,866,034 | A | 9/1989 | Ribi | |
| 4,877,611 | A | 10/1989 | Cantrell | |
| 4,912,094 | A | 3/1990 | Myers et al. | |
| 5,856,462 | A | 1/1999 | Agrawal | |
| 6,113,918 | A | 9/2000 | Johnson et al. | |
| 6,355,257 | B1 | 3/2002 | Johnson et al. | |
| 2011/0104293 | A1* | 5/2011 | Pulendran | A61K 39/07 424/490 |
| 2012/0058154 | A1* | 3/2012 | Ilyinskii | A61K 39/145 424/400 |
| 2014/0004193 | A1 | 1/2014 | Gourapura et al. | |
| 2014/0302120 | A1 | 10/2014 | Carson et al. | |

FOREIGN PATENT DOCUMENTS

| | | |
|---|---|---|
| CN | 104013955 | 9/2012 |
| WO | 94/00153 | 1/1994 |
| WO | 95/17210 | 6/1995 |
| WO | 96/02555 | 2/1996 |
| WO | 96/33739 | 10/1996 |
| WO | 99/33488 | 7/1999 |
| WO | 99/52549 | 10/1999 |
| WO | 00/09159 | 2/2000 |

OTHER PUBLICATIONS

Ali A, et al., 2015. Identification of swine H1N2/pandemic H1N1 reassortant influenza virus in pigs, United States. Vet Microbiol 158:60-68.
Almeida AJ, et al., 1996. Nasal delivery of vaccines. J Drug Target 3:455-467.
Arens R, et al., 2010. Plasticity in programming of effector and memory CD8 T-cell formation. Immunol Rev 235:190-205.
Babensee JE, et al., 2005. Differential levels of dendritic cell maturation on different biomaterials used in combination products. Journal of Biomedical Materials Research Part A 74A:503-510.
Baker et al., 1991. Structures of bovine and human papillomaviruses. Analysis by cryoelectron microscopy and three-dimensional image reconstruction. Biophys. J. 60:1445-1456.
Beaudette TT, et al., 2009. In vivo studies on the effect of co-encapsulation of CpG DNA and antigen in acid-degradable microparticle vaccines. Mol Pharm 6:1160-1169.
Binjawadagi B, e al., 2014. An innovative approach to induce cross-protective immunity against porcine reproductive and respiratory syndrome virus in the lungs of pigs through adjuvanted nanotechnology-based vaccination. Int J Nanomedicine 9:1519-1535.
Binjawadagi B., et al., 2014. Adjuvanted poly(lactic-co-glycolic) acid nanoparticle-entrapped inactivated porcine reproductive and respiratory syndrome virus vaccine elicits cross-protective immune response in pigs. Int J Nanomedicine 9:679-694.

(Continued)

*Primary Examiner* — Barry A Chestnut
(74) *Attorney, Agent, or Firm* — Meunier Carlin & Curfman LLC

(57) ABSTRACT

Disclosed herein are methods and compositions for treating or preventing swine influenza in a subject.

22 Claims, 21 Drawing Sheets

(56) References Cited

OTHER PUBLICATIONS

Blair DA, et al., 2011. Duration of antigen availability influences the expansion and memory differentiation of T cells. J Immunol 187:2310-2321.

Blank F, et al., 2013. Size-dependent uptake of particles by pulmonary antigen-presenting cell populations and trafficking to regional lymph nodes. Am J Respir Cell Mol Biol 49:67-77.

Bot A, et al., 1998. Protective Role of Gamma Interferon during the Recall Response to Influenza Virus. Journal of Virology 72:6637-6645.

CDC. 2009. "First Global Estimates of 2009 H1N1 Pandemic Mortality Released by CDC-Led Collaboration". Centers for Disease Control and Prevention (CDC). Jun. 25, 2012. Retrieved Jul. 3, 2012.

Chadwick S, et al., 2010. Nanotechnology solutions for mucosal immunization. Adv Drug Deliv Rev 62:394-407.

Chithrani B.D., et al., 2006. Determining the size and shape dependence of gold nanoparticle uptake into mammalian cells. Nano Lett 6:662-668.

Danhier F., et al., 2012. PLGA-based nanoparticles: an overview of biomedical applications. J Control Release 161:505-522.

Dawood F.S., 2012. Estimated global mortality associated with the first 12 months of 2009 pandemic influenza A H1N1 virus circulation: a modelling study. Lancet Infect Dis 12:687-695.

Dwivedi V., et al., 2012. Biodegradable Nanoparticle-Entrapped Vaccine Induces Cross-Protective Immune Response against a Virulent Heterologous Respiratory Viral Infection in Pigs. PLoS One 7:e51794.

Dwivedi V., et al., 2013. PLGA nanoparticle entrapped killed porcine reproductive and respiratory syndrome virus vaccine helps in viral clearance in pigs. Vet Microbiol 166:47-58.

Elamanchili P, et al., 2004. Characterization of poly(d,l-lactice-co-glycolic acid) based nanoparticulate system for enhanced delivery of antigens to dendritic cells. Vaccine 22:2406-2412.

Ellebedy A.H. et al., 2009. Influenza vaccines. Vaccine 27 Suppl 4:D65-68.

Foged C., et al., 2005. Particle size and surface charge affect particle uptake by human dendritic cells in an in vitro model. Int J Pharm 298:315-322.

Ganter M, Hensel A. 1997. Cellular variables in bronchoalveolar lavage fluids (BALF) in selected healthy pigs. Res Vet Sci 63:215-217.

Gauger P.C. et al., 2011. Enhanced pneumonia and disease in pigs vaccinated with an inactivated human-like (delta-cluster) H1N2 vaccine and challenged with pandemic 2009 H1N1 influenza virus. Vaccine 29:2712-2719.

Gerelchuluun T, et al., 2007. Dendritic cells process antigens encapsulated in a biodegradable polymer, poly(D,L-lactide-co-glycolide), via an alternate class I MHC processing pathway. Archives of Pharmacal Research 30:1440-1446.

Gerner W, et al., 2009. Porcine T lymphocytes and NK cells—An update. Dev Comp Immunol 33:310-320.

Greenway T.E., et al., 1998. Induction of protective immune responses against Venezuelan equine encephalitis (VEE) virus aerosol challenge with microencapsulated Vee virus vaccine. Vaccine 16:1314-1323.

Gregory A.E., et al., 2013. Vaccine delivery using nanoparticles. Front Cell Infect Microbiol 3:13.

Haden C., 2012. Assessing production parameters and economic impact of swine influenza, PRRS and Mycoplasma hyopneimoniae on finishing pigs in a large production system. Proceedings of the AASV Annual Meeting, 2012, 75-76.

Hagensee et al., 1994. Three-dimensional structure of vaccinia virus-produced human papillomavirus type 1 capsids. J. Virol. 68:4503-4505.

Hamdy S, et al., 2008. Co-delivery of cancer-associated antigen and Toll-like receptor 4 ligand in PLGA nanoparticles induces potent CD8+ T cell-mediated anti-tumor immunity. Vaccine 26:5046-5057.

Hanlon DJ, et al., 2011. Enhanced Stimulation of Anti-Ovarian Cancer CD8+ T Cells by Dendritic Cells Loaded with Nanoparticle Encapsulated Tumor Antigen. American Journal of Reproductive Immunology 65:597-609.

Hiremath et al., PLGA—Nanoparticle entrapped swine influenza virus peptides vaccine induces epitope specific cell-mediated immune response in pigs, CRWAD, At Chicago, Illinois., vol. 95th, 2014. Abstract.

Hiremath J., et al., 2016. Entrapment of H1N1 Influenza Virus Derived Conserved Peptides in PLGA Nanoparticles Enhances T Cell Response and Vaccine Efficacy in Pigs. PLoS One 11:e0151922.

International Preliminary Report ob Patentability issued for International Application No. PCT/US2016/034316, dated Dec. 7, 2017.

International Search Report and Written Opinion issued for International Application No. PCT/US2016/034316, dated Sep. 9, 2016.

Ito T., et al., 1998. Molecular basis for the generation in pigs of influenza A viruses with pandemic potential. J Virol 72:7367-7373.

Janke B.H., 2013. Clinicopathological features of Swine influenza. Curr Top Microbiol Immunol 370:69-83.

Jiang W, et al., 2005. Biodegradable poly(lactic-co-glycolic acid) microparticles for injectable delivery of vaccine antigens. Adv Drug Deliv Rev 57:391-410.

Jong S, et al., 2007. Encapsulation in liposomal nanoparticles enhances the immunostimulatory, adjuvant and anti-tumor activity of subcutaneously administered CpG ODN. Cancer Immunology, Immunotherapy 56:1251-1264.

Khatri M, et al., 2010. Swine influenza H1N1 virus induces acute inflammatory immune responses in pig lungs: a potential animal model for human H1N1 influenza virus. J Virol 84:11210-11218.

Kitikoon P., et al., 2009. Swine influenza matrix 2 (M2) protein contributes to protection against infection with different H1 swine influenza virus (SIV) isolates. Vaccine 28:523-531.

La Gruta NL, et al., 2014. T cell mediated immunity to influenza: mechanisms of viral control. Trends in Immunology 35:396-402.

Lambert LC, Fauci AS. 2010. Influenza vaccines for the future. N Engl J Med 363:2036-2044.

Liu Q, et al., 2015. Conjugating influenza a (H1N1) antigen to n-trimethylaminoethylmethacrylate chitosan nanoparticles improves the immunogenicity of the antigen after nasal administration. J Med Virol 87:1807-1815.

Mahapatro A., et al., 2011. Biodegradable nanoparticles are excellent vehicle for site directed in-vivo delivery of drugs and vaccines. Journal of Nanobiotechnology 9:1-11.

Makadia H.K., 2011. Poly Lactic-co-Glycolic Acid (PLGA) as Biodegradable Controlled Drug Delivery Carrier. Polymers (Basel) 3:1377-1397.

Manolova V, et al., 2008. Nanoparticles target distinct dendritic cell populations according to their size. European Journal of Immunology 38:1404-1413.

Mansoor F, et al., 2015. Comparing the immune response to a novel intranasal nanoparticle PLGA vaccine and a commercial BPI3V vaccine in dairy calves. BMC Veterinary Research 11:1-11.

McSorley et al., 2002. Bacterial Flagellin is an effective adjuvant for CD4+vTcell in vivo. J. Immunol. 169:3914-19.

Moss P. 2003. Cellular immune responses to influenza. Developments in biologicals 115:31-37.

Olin MR, et al., 2005. Gammadelta lymphocyte response to porcine reproductive and respiratory syndrome virus. Viral Immunol 18:490-499.

Organization WHO. 2014. Influenza (seasonal) fact sheet. http://www.who.int/mediacentre/factsheets/fs211/en/.

Panyam J, et al., 2002. Rapid endo-lysosomal escape of poly(DL-lactide-co-glycolide) nanoparticles: implications for drug and gene delivery. FASEB J 16:1217-1226.

Rawat A, et al., 2008. Inhalable large porous microspheres of low molecular weight heparin: in vitro and in vivo evaluation. J Control Release 128:224-232.

Reed LJ, Muench L. 1938. A Simple Method of Estimating Fifty Per Cent Endpoints. The American Journal of Hygiene 27(3):493-497.

Renukaradhya G.J., et al., 2010. Porcine reproductive and respiratory syndrome virus-induced immunosuppression exacerbates the inflammatory response to porcine respiratory coronavirus in pigs. Viral Immunol 23:457-466.

(56) References Cited

OTHER PUBLICATIONS

Richt J.A., et al., 2006. Vaccination of pigs against swine influenza viruses by using an NS1-truncated modified live-virus vaccine. J Virol 80:11009-11018.
Roos, Robert, 2011. Study puts global 2009 H1N1 infection rate at 11% to 21%. CIDRAP. Retrieved Aug. 10, 2011.
Saalmuller A, et al., 2002. T-helper cells from naive to committed. Vet Immunol Immunopathol 87:137-145.
Sato et al., 1996. Immunostimulatory DNA sequences necessary for effective intradermal gene immunization. Science 273:352-4.
Savic M, et al., 2016. Epitope specific T-cell responses against influenza A in a healthy population. Immunology 147:165-177.
Shen H, et al., 2006. Enhanced and prolonged cross-presentation following endosomal escape of exogenous antigens encapsulated in biodegradable nanoparticles. Immunology 117:78-88.
Shephard M.J., et al., 2003. Immunogenicity of bovine parainfluenza type 3 virus proteins encapsulated in nanoparticle vaccines, following intranasal administration to mice. Res Vet Sci 74:187-190.
Singh M, et al., 2001. A novel bioadhesive intranasal delivery system for inactivated influenza vaccines. J Control Release 70:267-276.
Talker SC, et al., 2013. Phenotypic maturation of porcine NK- and T-cell subsets. Dev Comp Immunol 40:51-68.
Thomas C., et al., 2011. Aerosolized PLA and PLGA Nanoparticles Enhance Humoral, Mucosal and Cytokine Responses to Hepatitis B Vaccine. Mol Pharm 8:405-415.
Thome M, et al., 1994. Porcine T-cell receptors: molecular and biochemical characterization. Vet Immunol Immunopathol 43:13-18.
Vincent A., et al., 2014. Review of Influenza A Virus in Swine Worldwide: A Call for Increased Surveillance and Research. Zoonoses and Public Health 61:4-17.
Vincent A.L., et al., 2008. Failure of protection and enhanced pneumonia with a US H1N2 swine influenza virus in pigs vaccinated with an inactivated classical swine H1N1 vaccine. Vet Microbiol 126:310-323.
Welsh RM, et al., 1997. $\alpha\beta$ and $\gamma\delta$ T-cell networks and their roles in natural resistance to viral infections. Immunological Reviews 159:79-93.
WHO HN. 2010. "H1N1 Still a Pandemic, Says WHO". redOrbit. Retrieved Aug. 10, 2010.
WHO. 2010. Pandemic (H1N1) 2009—update 100. Disease Outbreak News [World Health Organization (WHO)]. May 14, 2010. Archived from the original on May 18, 2010. Retrieved May 14, 2010.
Woodrow K.A., et al., 2012. Mucosal vaccine design and delivery. Annu Rev Biomed Eng 14:17-46.
Yang Y-W, et al., 2008. The effect of poly(d,l-lactide-co-glycolide) microparticles with polyelectrolyte self-assembled multilayer surfaces on the cross-presentation of exogenous antigens. Biomaterials 29:2516-2526.
Yassine H.M., et al., 2009. Characterization of triple reassortant H1N1 influenza A. viruses from swine in Ohio. Vet Microbiol 139:132-139.
Yassine H.M., et al., 2015. Hemagglutinin-stem nanoparticles generate. eterosubtypic influenza protection. Nat Med 21:1065-1070.
Yoshida M, Babensee JE. 2004. Poly(lactic-co-glycolic acid) enhances maturation of human monocyte-derived dendritic cells. J Biomed Mater Res A 71:45-54.
Yoshida M, et al., 2006. Differential effects of agarose and poly(lactic-co-glycolic acid) on dendritic cell maturation. J Biomed Mater Res A 79:393-408.
Yoshida M,et al., 2007. Effect of poly(lactic-co-glycolic acid) contact on maturation of murine bone marrow-derived dendritic cells. J Biomed Mater Res A 80:7-12.
Zaman M, et al., 2013. Nanovaccines and their mode of action. Methods 60:226-231.
Zhang Z, et al., 2011. Induction of anti-tumor cytotoxic T cell responses through PLGA-nanoparticle mediated antigen delivery. Biomaterials 32:3666-3678.
Zuckermann FA. 1999. Extrathymic CD4/CD8 double positive T cells. Vet Immunol Immunopathol 72:55-66.
Anonymous. "Vaxigrip—Influenza vaccine." Jan. 1, 2014. XP055528247, retrieved at https://www.aas.ru/file/Vaxigrip/pdf [retrieved on Nov. 28, 2018].
Coombes, A. G. A., et al. "Resorbable lamellar particles of polylactide as adjuvants for influenza virus vaccines." Biomaterials 19.11-12 (1998): 1073-1081.
Extended European Search Report and Search Opinion. Issued by the European Patent Office in Application No. EP 16800710.2 dated Dec. 12, 2018. 15 pages.
Hilbert, Anne K., Ulrike Fritzsche, and Thomas Kissel. "Biodegradable microspheres containing influenza A vaccine: immune response in mice." Vaccine 17.9-10 (1999): 1065-1073.
Ma, Wenjun, Robert E. Kahn, and Juergen A. Richt. "The pig as a mixing vessel for influenza viruses: human and veterinary implications." Journal of molecular and genetic medicine: an international journal of biomedical research 3.1 (2009): 158-166.
Mohajer, Maryam, Bahman Khameneh, and Mohsen Tafaghodi. "Preparation and characterization of PLGA nanospheres loaded with inactivated influenza virus, CpG-ODN and Quillaja saponin." Iranian journal of basic medical sciences 17.9 (2014): 722.
Moldoveanu, Z., et al. "Immune responses to influenza virus in orally and systemically immunized mice." New Strategies for Oral Immunization. Springer, Berlin, Heidelberg, 1989. 91-99.
Moldoveanu, Zina, et al. "Oral immunization with influenza virus in biodegradable microspheres." Journal of Infectious Diseases 167.1 (1993): 84-90.
Sandbulte, Matthew, et al. "Optimal use of vaccines for control of influenza A virus in swine." Vaccines 3.1 (2015): 22-73.
Weniger, Bruce G. "History of cutaneous administration of inactivated polio vaccine and novel devices for dose-sparing lelivery." Jan. 1, 2008. pp. 1-8. Retrieved from the Internet on Nov. 29, 2018, http://www.who.int/immunization_standards/vaaccine_quality/10_weniger_history_IPV.pdf.
Zhang, X. M., et al. "Detection of antibodies against human influenza A virus (H1N1) in swine sera in the Federal Republic of Germany." Journal of Veterinary Medicine, Series B 35.1-10 (1988): 474-476.
Knuschke, Torben, et al. "Immunization with biodegradable nanoparticles efficiently induces cellular immunity and protects against influenza virus infection." The Journal of Immunology 190.12 (2013): 6221-6229.
Sawaengsak, Chompoonuch, et al. "Chitosan nanoparticle encapsulated hemagglutinin-split influenza virus mucosal vaccine." AAPS PharmSciTech 15.2 (2014): 317-325.
Hu, Lei, et al. "Biophysical characterization and conformational stability of Ebola and Marburg virus-like particles." Journal of pharmaceutical sciences 100.12 (2011): 5156-5173.
Ausar, Salvador F., et al. "High-throughput screening of stabilizers for respiratory syncytial virus: identification of stabilizers and their effects on the conformational thermostability of viral particles." Human vaccines 3.3 (2007): 94-103.

\* cited by examiner

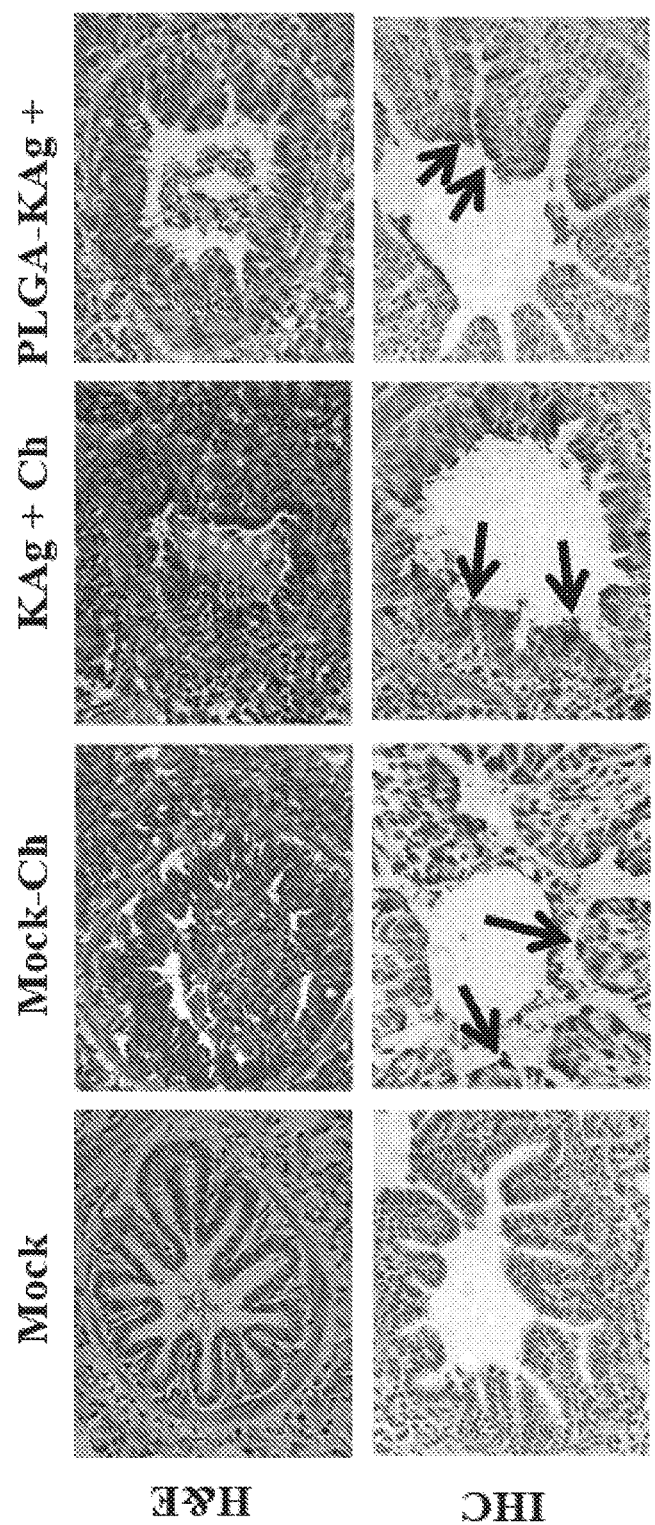

NANOPARTICLE BASED VACCINE STRATEGY AGAINST SWINE INFLUENZA VIRUS

CROSS-REFERENCE TO RELATED APPLICATIONS

This application is a national stage application filed under 35 U.S.C. of PCT/US2016/034316 filed May 26, 2016, which claims benefit of U.S. Provisional Application No. 62/166,344, filed May 26, 2015, which are hereby incorporated herein by reference in their entireties.

STATEMENT REGARDING FEDERALLY SPONSORED RESEARCH OR DEVELOPMENT

This invention was made with Government Support under Grant No. 2013-67015-20476 awarded by the National Institute of Food and Agriculture. The Government has certain rights in the invention.

BACKGROUND

Swine influenza is an acute respiratory infection of pigs caused by influenza A virus (IAV) of Orthomyxoviridae family. At present H1N1, H1N2 and H3N2 subtypes of IAV cause majority of infection in pigs. Owing to the presence of both avian ($\alpha2,3$ Gal) and human ($\alpha2,6$ Gal) IAV receptors, pigs can potentially act as mixing vessel for different IAV. Acute clinical signs in influenza infected pigs include high fever, anorexia, respiratory distress, nasal discharge and coughing. Influenza causes significant economic loss in the pig industry through morbidity, loss of body weight gain, increased time to market, susceptibility to secondary bacterial and viral infections like *mycoplasma* and porcine reproductive and respiratory syndrome (PRRS), medication and veterinary expenses. Some of the swine influenza virus (SwIV) can also be transmitted from pigs to humans creating public health risk. For example, the 2009 H1N1 swine influenza virus infected approximately 20% of the global population and caused around 200,000 deaths, in addition to approximately 500,000 deaths due to seasonal annual influenza infection.

Vaccination is one of the most effective means of controlling influenza. At present swine influenza vaccines are commercially available to use in pigs. Due to high mutation rates in circulating influenza viruses in animals the efficacy of commercial vaccines in the field is always poor. Commercial multivalent vaccines coadministered with an adjuvant intramuscularly as prime-boost strategy provide homologous, but weak heterologous protection. Intramuscular vaccination does not induce the required levels of local mucosal antibody and cellular immune responses; moreover, there are reports of inactivated vaccine associated enhanced respiratory disease. Thus, persistent economic burden of swine influenza in pig industry and its potential risk of zoonotic transmission to humans warrants the development of broadly cross-protective vaccine platforms.

SUMMARY

Disclosed herein are methods and compositions for treating or preventing swine influenza in a subject. In particular, disclosed herein is an immunogenic composition comprising an inactivated swine influenza A virus and a poly(lactide-co-glycolide) (PLGA) nanoparticle. In some embodiments, the composition and/or nanoparticle further comprises an adjuvant.

In some embodiments, the inactivated swine influenza A virus is an H1N1, H1N2 or H3N2 strain of swine influenza A virus.

Also disclosed is a vaccine comprising the disclosed immunogenic composition in a pharmaceutically acceptable carrier.

Also disclosed is a method of eliciting an immune response against swine influenza A virus in a pig comprising administering to the pig the disclosed vaccine.

In some embodiments, the vaccine is administered intranasally.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
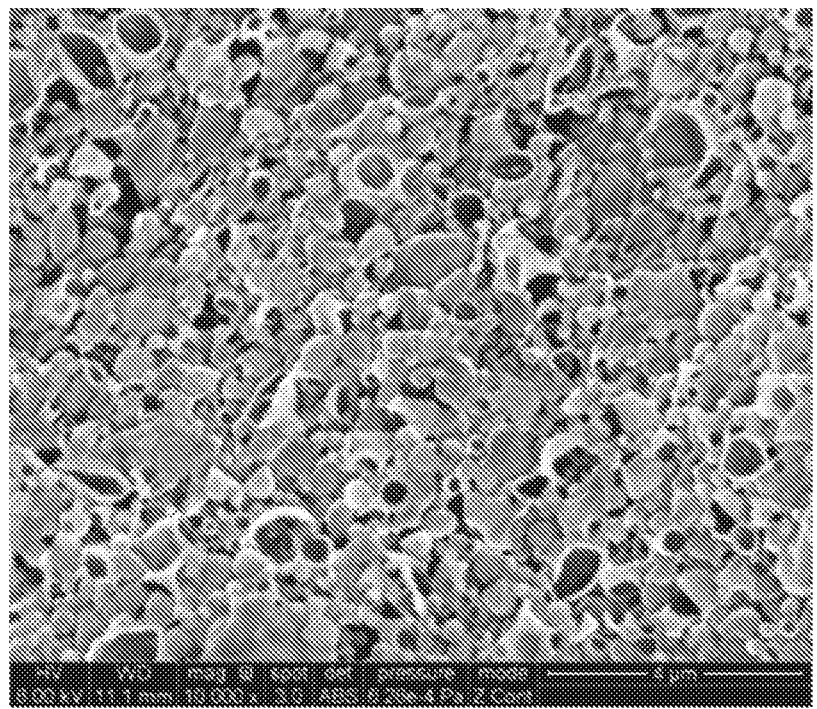
FIG. 1: In vitro physical characterization of PLGA-KAg NPs and their role in maturation of APCs. (A) Surface morphology of PLGA-KAg (10 K× magnification). (B) Size distribution of PLGA-KAg. Percentages were calculated based on determining the size of 200 NPs. (C) In vitro protein release profile of PLGA-KAg over a period of 4 weeks. Effect of treatment of PLGA-KAg on the expression of costimulatory molecule CD80/86 on pig (D) MoDCs and (E) macrophages. Data were analyzed by one way ANOVA followed by Tukey's post-hoc test. Asterisk refers to statistical significant difference between the two indicated pig groups (*$p<0.05$; $p<0.01$; and *$p<0.001$).

Disclosed herein are methods and compositions for treating or preventing swine influenza in a subject that involve combining inactivated swine influenza A virus with a nanoparticle.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

An "immunogenic composition" is a composition of matter suitable for administration to a human or animal subject (e.g., in an experimental setting) that is capable of eliciting a specific immune response, e.g., against a pathogen, such as swine influenza A virus. As such, an immunogenic composition includes one or more antigens (for example, whole purified virus or antigenic subunits, e.g., polypeptides, thereof) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or treated, e.g., reduced or ameliorated) by inhibiting replication of the pathogen following exposure of the subject to the pathogen. In the context of this disclosure, the term immunogenic composition will be understood to encompass compositions that are intended for administration to a subject or population of subjects for the purpose of eliciting a protective or palliative immune response against the virus (that is, vaccine compositions or vaccines).

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule). An antigen can also affect the innate immune response.

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ T cell response or a CD8+ T cell response. In some cases, the response is specific for a particular antigen (that is, an "antigen-specific response"). An immune response can also include the innate response. If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

The immunogenic compositions disclosed herein are suitable for preventing, ameliorating and/or treating disease caused by infection of the virus.

The abbreviation "KAg" stands for killed antigen and represents the killed or inactivated virus. The inactivated virus comprises one or more immunogenic viral proteins and therefore the inactivated virus can be considered a killed antigen.

The abbreviation "NP-KAg" stands for nanoparticle-killed antigen. This represents the nanoparticle encapsulated inactivated swine influenza virus.

As used herein, the terms "virus-like particle" or "VLP" refer to a non-replicating, viral shell. VLPs are generally composed of one or more viral proteins associated with viral surface capsid structure. VLPs can form spontaneously upon recombinant expression of the protein in an appropriate expression system. VLPs, when administered to an animal, can be immunogenic and thus can cause a protective or therapeutic immune response in the animal. Methods for producing VLPs are generally known in the art and discussed more fully below. The presence of VLPs following recombinant expression of viral proteins can be detected using conventional techniques known in the art, such as by electron microscopy, biophysical characterization, and the like. See, e.g., Baker et al., Biophys. J. (1991) 60:1445-1456; Hagensee et al., J. Virol. (1994) 68:4503-4505. For example, VLPs can be isolated by density gradient centrifugation and/or identified by characteristic density banding.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The compositions, immunogenic compositions and vaccines described herein can comprise one or more nanoparticles. Examples of nanoparticles (used interchangably with the term "nanocarrier") include, but are not limited to nanocarriers composed of one or more polymers. In some embodiments, the one or more polymers is a water soluble, non-adhesive polymer. In some embodiments, polymer is polyethylene glycol (PEG) or polyethylene oxide (PEO). In some embodiments, the polymer is polyalkylene glycol or polyalkylene oxide. In some embodiments, the one or more polymers is a biodegradable polymer. In some embodiments, the one or more polymers is a biocompatible polymer that is a conjugate of a water soluble, non-adhesive polymer and a biodegradable polymer. In some embodiments, the biodegradable polymer is polylactic acid (PLA), poly(glycolic acid) (PGA), or poly(lactic acid/glycolic acid) (PLGA). In some embodiments, the nanocarrier is composed of PEG-PLGA polymers.

In some embodiments, the nanocarrier is formed by self-assembly. Self-assembly refers to the process of the formation of a nanocarrier using components that will orient themselves in a predictable manner forming nanocarriers predictably and reproducibly. In some embodiments, the nanocarriers are formed using amphiphillic biomaterials which orient themselves with respect to one another to form nanocarriers of predictable dimension, constituents, and placement of constituents. In some embodiments, the nanocarrier is a microparticle, nanoparticle, or picoparticle. In some embodiments, the microparticle, nanoparticle, or picoparticle is self-assembled.

In some embodiments, the nanocarrier has a positive zeta potential. In some embodiments, the nanocarrier has a net positive charge at neutral pH. In some embodiments, the nanocarrier comprises one or more amine moieties at its surface. In some embodiments, the amine moiety is a primary, secondary, tertiary, or quaternary amine. In some embodiments, the amine moiety is an aliphatic amine. In some embodiments, the nanocarrier comprises an amine-containing polymer. In some embodiments, the nanocarrier comprises an amine-containing lipid. In some embodiments, the nanocarrier comprises a protein or a peptide that is positively charged at neutral pH. In some embodiments, the nanocarrier is a latex particle. In some embodiments, the nanocarrier with the one or more amine moieties on its surface has a net positive charge at neutral pH.

Nanoparticles can aid the delivery of the inactivated swine influenza A virus and/or can also be immunogenic. Delivery can be to a particular site of interest, e.g. the mucosa. In some embodiments, the nanoparticle can create a timed release of the inactivated swine influenza A virus to enhance and/or extend the immune response. In some embodiments, the nanoparticle is associated with the inactivated swine influenza A virus such that the composition can elicit an immune response. The association can be, for example, wherein the nanoparticle is entrapped or encapsulated with the inactivated swine influenza A virus. By entrapped is meant that there is a physical encasing the inactivated swine influenza A virus in nanoparticles. In some embodiments, the inactivated swine influenza A virus is entrapped within the nanoparticle by a water/oil/water emulsion method. In some embodiments, the nanoparticle is poly(lactide co-glycolide) (PLGA). Depending on the ratio of lactide to glycolide used for the polymerization, different forms of PLGA can be obtained and utilized. These forms are typically identified in regard to the monomers' ratio used (e.g. PLGA 75:25 identifies a copolymer whose composition is 75% lactic acid and 25% glycolic acid). Different ratios can be used in this invention, e.g. 90:10, 80:20, 70:30, 60:40, 50:50, 40:60, 30:70, 20:80, 10:90, and numbers above and in between these ratios. Additional examples of suitable nanoparticles include chitosin, calcium phosphate, lipids of various bacteria like *E. coli*, mycobactera, leptospira and mixtures thereof. In one example, the composition can be derived mixing about 180 mg of PLGA to about 5 mg of inactivated swine influenza A virus (or about 36 mg PLGA to 1 mg inactivated swine influenza A virus). The entrapment (encapsulation) efficiency of inactivated swine influenza A virus can vary. In one embodiment the nanoparticle were 50-55% entrapped/encapsulated, calculated based on amount of total swine influenza A virus protein used in the entrapment. Entrapped inactivated swine influenza A virus can be administered as mixtures of entrapped/encapsulated and unentrapped/unencapsulated antigens or the entrapped/encapsulated antigens can be further purified.

In some embodiments, the antigen is derived from inactivated or killed swine influenza A virus. In one embodiment, the swine influenza A virus is inactivated or killed by UV light. Other means of inactivation include chemical, heat, or radioactivity.

Any suitably immunogenic inactivated swine influenza A virus or swine influenza A virus antigen can be utilized in the composition. For example, the swine influenza A virus antigen can be a swine influenza A virus surface glycoprotein. Examples of immunogenic antigens include recombinantly derived hemagglutinin, neuraminidase, nucleocapsid and matrix proteins. The swine influenza A virus antigen can be recombinantly derived.

Disclosed are compositions comprising virus-like particles (VLPs) and a nanoparticle. The disclosed compositions can comprise a VLP that is immunogenic. VLPs resemble viruses, but are non-infectious because they do not contain any viral genetic material. The expression of viral structural proteins, such as Capsid, can result in the self-assembly of VLPs. VLPs can be produced in a variety of cell culture systems including mammalian cell lines, insect cell lines, yeast, and plant cells. For example, the VLP can be produced by a baculovirus or a plant system. The VLP can be immunogenic. Any of the disclosed nanoparticles can be used to entrap the swine influenza A virus VLP. For example, disclosed are swine influenza A virus VLPs entrapped in PLGA nanoparticles.

Described herein are vaccines comprising an immunogenic composition disclosed herein in a carrier wherein the vaccine is protective against swine influenza A virus infection. The term "immunogenic carrier" as used herein can refer to a first polypeptide or fragment, variant, or derivative thereof which enhances the immunogenicity of a second polypeptide or fragment, variant, or derivative thereof. An "immunogenic carrier" can be fused, to or conjugated/coupled to the desired polypeptide or fragment thereof. See, e.g., European Patent No. EP 0385610 B1, which is incorporated herein by reference in its entirety for its teaching of fusing, conjugating or coupling a polypeptide to a carrier. An example of an "immunogenic carrier" is PLGA. In some embodiments the vaccine can comprise whole virus inactivated swine influenza A virus, encapsulated by PLGA, and a carrier.

Disclosed are illustrative immunogenic compositions, e.g., vaccine compositions. Additionally, the compositions described herein can comprise one or more immunostimulants. An immunostimulant refers to essentially any substance that enhances or potentiates an immune response (antibody or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS-2 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions.

Optionally, the adjuvants used in conjunction with the disclosed compositions increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. The level of Th2-type cytokines can increase to a greater extent than the level of Th1-type cytokines.

Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.; see, for example, U.S. Pat. Nos. 4,436,727; 4,877,611; 4,866,034 and 4,912,094, which are hereby incorporated by reference for their teaching of the same). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato el al., Science 273:352, 1996. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other formulations can include more than one saponin in the adjuvant combinations, for example combinations of at least two of the following group comprising QS21, QS7, Quil A, β-escin, or digitonin.

Saponin formulations can also be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins can also be formulated in the presence of cholesterol to form particulate structures such as liposomes or immune-stimulating complexes (ISCOMs). Furthermore, the saponins may be formulated together with a polyoxyethylene ether or ester, in either a non-particulate solution or suspension, or in a particulate structure such as a paucilamelar liposome or ISCOM. The saponins can also be formulated with excipients such as CARBOPOL™ (Noveon, Cleveland, Ohio) to increase viscosity, or may be formulated in a dry powder form with a powder excipient such as lactose.

Optionally, the adjuvant system includes the combination of a monophosphoryl lipid A and a saponin derivative, such as the combination of QS21 and 3D-MPL adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Optionally the formulation additionally comprises an oil in water emulsion and tocopherol.

Additional illustrative adjuvants for use in the disclosed compositions Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (Enhanzyn™) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Described herein are methods of eliciting an immune response against swine influenza A virus in a pig comprising administering to the pig a composition disclosed herein. The immune response can be protective. The method can further comprise administering to the pig virulent swine influenza A virus to monitor the vaccine efficacy.

Described herein are methods of reducing reproductive or respiratory failure in pigs comprising administering a vaccine or composition disclosed herein to pigs. The method can further comprise administering to the pig virulent swine influenza A virus to monitor the vaccine efficacy. Also described are methods of stimulating an immune response in a pig comprising: administering to the pig a vaccine or composition provided herein.

Also described are methods and compositions that can be used to increase (e.g. 0.5, 1, 2, 3, 4, 5, 6, 7, 8, 9, 10, 15, 20, 30 etc. fold increased) humoral and cell-mediated immune response to swine influenza A virus compared to killed swine influenza A virus vaccine antigens (K-Ag) in immunized homologous virus challenged pigs. The methods and compositions described herein can also be used to provide a significant increase (e.g. 0.5, 1, 2, 3, 4, 5, 6, 7, 8, 9, 10, 15, 20, 30 etc. fold increased) in virus neutralizing antibodies and IgA response in the lungs and blood when compared to killed swine influenza A virus vaccine antigens (K-Ag) in immunized, homologous virus challenged pigs. The methods and compositions described herein can also be used to provide lung lysate and serum of Nano-KAg vaccinated pigs with higher levels (e.g. 0.5, 1, 2, 3, 4, 5, 6, 7, 8, 9, 10, 15, 20, 30 etc. fold increased) of IFN-γ and IL-12, and lower levels of immunosuppressive mediators (IL-10 and TGF-β) (e.g. 0.5, 1, 2, 3, 4, 5, 6, 7, 8, 9, 10, 15, 20, 30 etc. fold decreased) compared to control pig groups. The methods and compositions described herein can also be used to provide mononuclear cells from the lungs, blood, BAL, TBLN, and blood of Nano-KAg vaccinated pigs having increased frequencies (e.g. 0.5, 1, 2, 3, 4, 5, 6, 7, 8, 9, 10, 15, 20, 30 etc. fold increased) of $CD4^+$, $CD8^+$, $CD4^+CD8^+$ T cells, γδ T cells, myeloid cells, and dendritic cells rich fractions. The methods and compositions can also be used to provide a decrease (e.g. 0.5, 1, 2, 3, 4, 5, 6, 7, 8, 9, 10, 15, 20, 30 etc. fold decreased) in $Foxp3^+$ T-regulatory cells. The compositions and methods can also be used to provide intranasal delivery of PLGA nanoparticle-entrapped swine influenza A virus killed vaccine that elicits an immune response at both mucosal and systemic sites sufficient to clear the viremia in pigs.

Also provided are the composition and methods than can be used to provide protective systemic and mucosal immune responses against swine influenza A virus that can clear the viremia early post-infection, e.g. three, two, and one week post infection (including 1, 2, 3, 4, 5, 6, 7, 8, 9, 10, 15, 20, 25, 30 days).

The vaccine or composition can also be administered at a dose, for example, of between 100 µg/pig and 1 mg/pig. Other examples include doses comprising 50 µg/pig and 500 µg/pig. The composition or vaccine can be administered for example in a single dose, or in two or more doses. In one embodiment, the two doses are administered at a two week interval. The composition or vaccine can, for example, be administered intranasally. Additional examples of alternative routes of immunization include intramuscular, subcutaneous, intranasal drops, and intranasal aerosol delivery.

The compositions and methods can also be used at a dose of vaccine or immunogen having less than $1\times10^8$ $TCID_{50}$ of swine influenza A virus. Also provided is a dose less than $1\times10^7$, $1\times10^6$, and $1\times10^5$ $TCID_{50}$ of swine influenza A virus. Further disclosed herein, each dose can be approximately $5\times10^6$ $TCID_{50}$ of swine influenza A virus. Also provided are examples of doses between $1\times10^8$ $TCID_{50}$ of swine influenza A virus and $1\times10^5$ $TCID_{50}$ of swine influenza A virus, between $1\times10^7$ and $1\times10^5$ $TCID_{50}$ of swine influenza A virus, between $1\times10^6$ and $5\times10^6$ $TCID_{50}$ of swine influenza A virus. The doses can be derived from UV treated swine influenza A virus. The doses can be administered as a single reduced viral dose to elicit a protective immune response.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Biodegradable Nanoparticle Delivery of Inactivated Swine Influenza Virus Vaccine Provides Heterologous Protection Through Cell-Mediated Immunity in Pigs Materials and Methods Cells and Viruses:

A stable *mycoplasma*-free Madin-Darby canine kidney epithelial cells (MDCK, CRL-2285, ATCC, VA) were maintained in Dulbecco's modified eagle medium (DMEM) (Gibco) supplemented with 10% fetal bovine serum (Sigma) and antibiotic-antimycotic (Gibco) at 37° C. in 5% $CO_2$ incubator. Field isolates of swine influenza virus (SwIV), SW/OH/FAH10-1/10 (H1N2-δ1 lineage) (Ali A, et al. 2012. Vet Microbiol 158:60-68) and SW/OH/24366/2007 (H1N1-γ) (Yassine H M, et al. 2009. Vet Microbiol 139:132-139) were used in inactivated virus vaccine preparation and challenge infection of pigs, respectively. The H1N2 virus (SW/OH/FAH10-1/10) has NP and M genes derived from the 2009 pandemic H1N1 (Ali A, et al. 2012. Vet Microbiol 158:60-68), and the A/swine/Ohio/24366/07 was a zoonotic virus isolated from swine and also was shown at the CDC to have 100% identical genome sequence to the human virus associated in the Ohio county fair (Yassine H M, et al. 2009. Vet Microbiol 139:132-139). SwIV stocks (passage 3) were obtained from the repository at FAHRP, Wooster, Ohio. Both viruses were propagated on MDCK cells by infecting at MOI 0.005 and maintaining in serum free DMEM supplemented with 1 µg/ml TPCK-trypsin (Sigma, MO).

Vaccine Preparation:

SwIV isolate SW/OH/FAH10-1/10 (H1N2-61) culture fluid was harvested and clarified to remove cell debris by centrifugation at 2000×g for 30 min and subjected to 10-fold concentration using Pellicon-2 cassette filtration (Millipore, MA) followed by ultra-centrifugation using Optima™ L-100XP ultracentrifuge (Beckman Coulter) with 20% sucrose cushion at 107,000×g for 4 hrs without break. Virus pellet was suspended in PBS containing protease inhibitor (Sigma, MO), titrated and stored at −80° C. Virus was inactivated using binary ethyleneimine (BEI) (Sigma, MO) by treating with 10 mM BEI for 6 hrs at 37° C. followed by treatment with 10 mM sodium thiosulphate (Sigma, MO) for additional 2 hrs at 37° C. to neutralize the unused BEI, and the virus inactivation was confirmed in MDCK cells. Total protein concentration in the virus pellet was estimated using micro BCA protein assay kit (Thermo Scientific, MA) as per the manufacturer's protocol.

Inactivated SwIV antigen (KAg) was encapsulated in PLGA-NPs by water/oil/water double emulsion solvent evaporation technique as described previously (Binjawadagi B, et al. 2014. Int J Nanomedicine 9:679-694; Hiremath J, et al. 2016. PLoS One 11:e0151922). Briefly, 5 mg of KAg in 500 µl PBS and 250 µl of 2% (w/v) polyvinyl alcohol (PVA) with protein stabilizers, 50 µl of 20% sucrose (w/v) and 50 µl of 20% $Mg(OH)_2$ (w/v), were emulsified in 180 mg of PLGA polymer solution in 4.5 ml of dichloromethane using high intensity ultrasonic processor (Sonics and Materials Inc., CT) for 30 sec at duty cycle 30% and output control 3. The resulting water-in-oil (w/o) primary emulsion was poured into a mixture of 23 ml 2% w/v PVA (Sigma) and 2 ml 12.5% (w/v) polaxmer 188 (Sigma, MO) to form an aqueous solution. The mixture was divided equally into two tubes and emulsified again by sonication for 60 sec to obtain secondary w/o/w emulsion, and it was emulsified by magnetic stirring overnight at 400 rpm in cold (4° C.) to allow evaporation of the organic solvents. Resulting polymeric particles were washed thrice using cold sterile Milli-Q water by centrifugation at 10,976×g (Beckman Coulter, FX6100 rotor) for 30 min. Finally, PLGA-NP pellet was suspended in 5% sucrose in milli Q water, frozen at −80° C., freeze-dried (Labconco, MO) for 18-20 hrs and aliquots were stored at −20° C. The inactivated KAg encapsulated in PLGA-NP is henceforth called as PLGA-KAg.

Characterization of PLGA-KAg:

Particle size and morphology was examined by a FEI Quanta 250 scanning electron microscope (SEM, Kyoto, Japan) after coating with 2 nm of iridium using a Quorum Q150TS sputter coater (Lewes, UK). Nanoparticle size distribution was characterized using ImageJ image software (National Institutes of Health, MD) with an average of 200 nanoparticles per image. Quasi-elastic light scattering experiments (QELS) were used to measure the ζ-potential of the nanoparticles using a Zetasizer Nano (Malvern Instruments Ltd., Worchester, UK). NPs 100 µg were suspended in cold nanopure water and thoroughly dispersed using a probe sonicator (Ultra Sonic Processor VC 130PB, Sonics Vibra Cell, CT) before analysis. Three independent measurements were taken in order to get an average ζ-potential value. Protein encapsulation efficiency and in vitro protein release profile at days 0, 1, 3, 5, 7, 10, 15, 20, 25 and 30 were estimated and expressed as the cumulative percentage release of SwIV antigens at each time point using the methods described previously (Binjawadagi B, et al. 2014. Int J Nanomedicine 9:679-694; Hiremath J, et al. 2016. PLoS One 11:e0151922).

In Vitro Activation of APCs by PLGA-K4g:

Isolated peripheral blood mononuclear cells (PBMCs) and bronchoalveolar lavage fluid (BAL) cells from healthy influenza free 2 month old pigs were used in in vitro experiments to characterize PLGA-KAg. To generate monocyte derived DCs (MoDCs), $CD172^+$ cells from PBMCs were magnetically sorted and treated with cytokines GM-CSF (50 ng/ml) and IL-4 (25 ng/ml) (Kingfisher biotech, MN) for a week. BAL cells (0.5 million) and MoDCs (0.1 million) were cultured with: (i) RPMI enriched with 10% FBS (E-RPMI) only; (ii) KAg (2 µg/ml) in E-RPMI; (iii) PLGA-KAg (KAg 2 µg/ml equivalent of NPs); or (iv) PLGA-NPs (equivalent weight of NPs) in E-RPMI for 24 hrs at 37° C. in a 5% $CO_2$ incubator. Stimulated cells were fixed and immunostained using CD172a and CD80/86 antibodies, and 50,000 events were acquired by flow cytometry (BD FACS Aria II, BD Pharmingen CA) and analyzed using the FlowJo software ((Tree Star, OR).

Experimental Design, Vaccination, Viral Challenge and Collection of Samples:

Caesarian delivered colostrum deprived (CDCD) and bovine colostrum fed Large White-Duroc crossbred 4-5 weeks old piglets (n=32) were raised in our BSL2 facility at OARDC as described previously (Hiremath J, et al. 2016. PLoS One 11:e0151922) and used in our study. Piglets were confirmed seronegative for hemagglutination (HI) antibodies against influenza virus subtypes H1N1 and H1N2 and were randomly divided into 4 experimental groups (n=7-9 pigs/group) (Table 1). Pigs were maintained, inoculated and euthanized in accordance with the standards of the Institutional Laboratory Animal Care and Use Committee at The Ohio State University. Animals were vaccinated at 4-5 weeks, boosted after 3 weeks and challenged after 2 weeks of boost. Pigs were vaccinated with $10^7$ $TCID_{50}$ equivalent of H1N2 KAg or PLGA-KAg suspended in 2 ml DMEM and delivered intranasally as a mist using a multidose delivery device (Prima Tech USA, NC) (FIG. 3A), and challenged using the heterologous H1N1 SwIV ($6 \times 10^6$ $TCID_{50}$) in 2 ml, 1 ml administered intranasally and another 1 ml intratracheally (Yassine H M, et al. 2009. Vet Microbiol 139:132-139).

Plasma samples were collected at days post-vaccination (DPV) 0, 21 and 35. From the day of challenge to euthanasia, pigs were observed twice daily for clinical signs and rectal temperature was recorded daily. Nasal swab samples were collected at days post-challenge (DPC) 4 and 6 in 2 ml DMEM containing antibiotics. Pigs were euthanized at DPC 6 and during necropsy the lungs were examined and scored for the gross lesions (Khatri M, et al. 2010. J Virol 84:11210-11218). Blood and BAL fluid samples were collected and aliquots of plasma and BAL fluid stored at −80° C. BAL fluid was collected by infusing 20 ml PBS (containing 2% EDTA) through the trachea and collected the fluid after gentle massaging of all the lung lobes. For preparation of lung lysate, 1 µm of lung tissue from the right apical lobe was homogenized in 3 ml DMEM (with protease inhibitor) and supernatant was collected after centrifugation and aliquots were stored at −80° C. as described previously (Renukaradhya G J, et al. 2010. Viral Immunol 23:457-466). Lung tissues were fixed in 10% neutral buffered formalin for histopathological and immunohistochemical evaluations. PBMCs were isolated at DPC 0 and 6 and used in cell proliferation assays upon stimulation with SwIV as well as used in flow cytometry analysis Cell Proliferation and Flow Cytometry Assays:

At DPC 0 antigen specific T cells proliferation was carried out in PBMCs using cell titer 96 aqueous non-radioactive proliferation assay kit (Promega, WI) as per the manufacturer's instructions. Briefly, $1 \times 10^6$ PBMCs/well were plated in a 96 well U-bottom plate (Greiner bio-one, NC) in 100 µl of E-RPMI medium. Both the SwIV H1N2 and H1N1 used in the vaccine preparation and pig challenge, respectively, were used at MOI of 0.1 in 100 µl ($1 \times 10^5$ TCID$_{50}$/well) for stimulation. Plates were incubated at 37° C. in a 5% CO$_2$ incubator, and after 72 hrs plates were centrifuged at 2000 rpm for 2 min and the supernatant was collected, and added 100 µl E-RPMI and 20 µl MTS+PMS solution to the cell pellet and incubated for another 4 hrs at 37° C. in a 5% CO$_2$ incubator. The optical density (OD) at 490 nm was recorded using the ELISA plate reader (Spectramax plus384, Molecular Devices, CA). Stimulation index (SI) was determined by dividing OD of stimulated PBMCs from OD of cell control of the same pig, and average SI values of 7 to 9 pigs of each group were compared among each other. At DPC 0 unstimulated PBMCs were also evaluated to determine the frequency of different T cell subsets by flow cytometry analysis.

At DPC6 PBMCs of pigs were re-stimulated with SwIV H1N2 and H1N1 at MOI 0.1 and subjected to cell proliferation as described above. The supernatant harvested from 72 hrs of restimulated PBMCs culture were analyzed for IFN-T by ELISA, and cells were subjected to immunophenotyping and analyzed by flow cytometry to determine the frequency of activated T cell subsets as described previously (Hiremath J, et al. 2016. PLoS One 11:e0151922). Briefly, PBMCs were blocked with 2% pig serum and surface-labeled with pig lymphocyte specific purified, fluorochrome or biotin conjugated mAbs followed by treatment with fluorochrome labeled anti-mouse isotype specific or streptavidin antibody. For intracellular IFNγ staining, GolgiPlug™ (BD Biosciences, CA) and Brefeldin A (Sigma, MO) were added during the last 6 hrs of incubation of PBMCs treated with or without indicated stimulants. The surface immunostained cells were fixed with 1% paraformaldehyde and permeabilized with cell-permeabilization buffer (85.9%0 deionized water, 11% PBS without Ca$_2^+$ or Mg$_2^+$, 30% formaldehyde solution, and 0.1% saponin) overnight at 4° C. Cells were washed and immunostained using fluorochrome-conjugated anti-pig IFNγ or its isotype control mAb (BD Biosciences, CA) in 0.1% saponin containing fluorescence-activated cell-sorting (FACS) buffer. Immunostained cells were acquired using the flow cytometer BD Aria II (BD Biosciences, CA) and analyzed using the FlowJo software (Tree Star, OR). All specific cell population frequencies were presented as the percent of total CD3$^+$/CD3$^+$ lymphocytes. Antibodies used in the flow cytometry were: anti-porcine CD3 (Southernbiotech, AL), CD4α (Southernbiotech, AL), CD8α (Southernbiotech, AL), CD83 (BD Biosciences, CA), δ-chain (BD Pharmingen, CA), monocyte/granulocyte antibody (CD172a, Southernbiotech, AL) and CD152-muIg (Ancell, MN).

Virus Titration:

Serial 10-fold dilutions of test samples in serum-free DMEM containing TPCK-trypsin (1 µg/ml) in quadruplicates were transferred to monolayer of MDCK cells cultured overnight in 96 well cell culture plates. Plates were incubated for 48 hrs at 37° C. in a 5% CO$_2$ incubator and fixed using 80% acetone in water and immunostained using IAV nucleoprotein specific primary antibody (#M058, CalBioreagents, CA) followed by Alexa Fluor 488 conjugated goat anti-mouse IgG (H+L) antibody (Life technologies, OR). Immunofluorescence was recorded using fluorescent microscope (Olympus, NY) and infectious virus titer was calculated using Reed and Muench method (Reed L J, et al. 1938. The American Journal of Hygiene 27(3):493-497).

Antibody Titration:

Hemagglutination inhibition (HI) titers and specific antibody levels were determined as described previously (Hiremath J, et al. 2016. PLoS One 11:e0151922). Briefly, HA units of SwIV H1N1 was first determined and the virus stock was diluted to get 8 HA units in 50 µl volume and used in a standard HI assay. Plasma and BAL fluid samples were incubated at 56° C. for 30 min to inactivate innate complement activity. The starting dilution of plasma and BAL fluid for HI assay was 1:2. SwIV specific IgG and IgA antibodies in nasal swab, BAL fluid, lung lysate and plasma samples were determined by ELISA. Briefly, flat bottom high binding 96 well plates (Greiner bio-one, NC) were coated with semipurified pretitrated SwIV H1N1 or H1N2 antigens (5 µg/ml) and incubated at 4° C. overnight. Plates were blocked with 5% skim milk in PBST for 2 hrs at RT and washed three times with PBST. Samples diluted in 2.5% skim milk were added 50 µl/well in duplicate and incubated at RT for 2 hrs. After three washes goat anti-pig IgA conjugated with HRP (Bethyl Laboratories Inc., TX) or goat anti-pig IgG (γ) conjugated with HRP (KPL, MD) was added at 50 µl/well (both the antibodies were diluted at 1:1000 in 2.5% skim milk in PBST) and incubated at RT for 2 hrs. The Ag-Ab reaction was developed calorimetrically by adding 1:1 mixture of peroxidase substrate solution B and TMB peroxidase substrate (KPL, MD) 50 µl/well. The reaction was stopped after 10-20 min by adding IM phosphoric acid (50 µl/well). Optical density (OD) was measured at 450 nm using the Spectramax microplate reader, and corrected OD value was obtained after subtracting blank OD from mean OD of different treatment groups. Virus neutralization titer (VNT) in BAL fluid was determined using the procedures described previously (Hiremath J, et al. 2016. PLoS One 11:e0151922).

Histopathology and Immunohistochemistry Analyses:

Five µm sections of apical, cardiac and diaphragmatic lung lobes of pigs were stained with hematoxylin and eosin and examined microscopically for histopathological changes as described previously (Khatri M, et al. 2010. J Virol 84:11210-11218). Peri-bronchial and perivascular accumulation of mononuclear inflammatory cells (MNCs) as well as bronchial exudates composed of dead sloughed epithelial cells and MNCs were scored as follows: 0, no change from normal; 0.5, changes present but too mild; 1, minimal changes from normal; 2, moderate changes from normal; and 3, marked changes from normal. Final lung pathology score for each pig was determined by taking the average of scores from the three lung lobes and the group averages were compared.

SwIV specific antigen in the lungs was detected by IHC method as described previously (Dwivedi V, et al. 2012. PLoS One 7:e51794; Richt J A, et al. 2006. J Virol 80:11009-11018) with a few modifications. Briefly, 5 µm tissue sections were deparaffinized and hydrated in Dulbecco's PBS (D-PBS) and incubated in 0.05% sodium borohydride solution for 10 min to break aldehyde bonds, washed twice and incubated in Protease VII (diluted 1:6.5 with D-PBS) for 30 min at RT for antigen retrieval. Slides were washed thrice and quenched in 3% $H_2O_2$ solution for 5 min, followed by three washes slides were blocked by incubating with 4% normal horse serum for 20 min at RT. Further, slides were incubated with SwIV nucleoprotein specific antibody (#MO58, CalBioreagents, CA) for 60 min at RT, washed thrice, and incubated with biotinylated secondary antibody for 60 min at RT. To detect positive signals, slides were incubated in VECTASTAIN elite ABC reagent (#PK-7100, Vector Lab., CA) followed by treatment with ImmPACT™ DAB Substrate (#SK-4105, Vector Lab., CA) as per manufacturer's instructions. The slides were rinsed in tap water, counterstained with hematoxylin, rinsed well in tap water, dehydrated and mounted. Positive IHC signals on bronchial epithelium of apical, cardiac and diaphragmatic lung lobes were scored according to the following criteria: 0, no changes comparable to mock control—normal; 0.5, suggestive but not definite; 1, minimal changes from normal; 2, moderate changes from normal; and 3, marked changes from normal. IHC score for each pig was determined by taking the average of scores from all three lung lobes and treatment pig group averages were compared. Microscopic and IHC slides were read by a board certificated veterinary pathologist who was blinded to the experimental design and SwIV infection status.

Ethics Statement:

This study was carried out in strict accordance with the recommendations by the Public Health Service Policy, USDA Regulations, National Research Council's Guide for the Care and Use of Laboratory Animals and the Federation of Animal Science Societies' Guide for the Care and Use of Agricultural Animals in Agricultural Research and Teaching. All the pigs were maintained, samples collected and euthanized, and all efforts were made to minimize the suffering of pigs as per the approved institutional, state and federal regulations and policies regarding animal care and use at The Ohio State University on the Ethics for Animal Experiments (Protocol Number: 2014A00000099).

Statistical Analysis:

Data were presented as mean±standard error of mean (SEM) of 7-9 pigs. For virus titer, titers of 100 were used for less than $10^1$ values; transformed to a $\log_{10}$ scale and analyzed (Dwivedi V, et al. 2013. Vet Microbiol 166:47-58). In each assay, the differences of means among the groups were determined by one-way analysis of variance (ANOVA) followed by Tukey's post-hoc comparison test in GraphPad Prism 5 (GraphPad Software, Inc., CA). A p-value less than 0.05 was considered statistically significant.

Results

In Vitro Characterization of PLGA-KAg NPs.

Figure 1B:
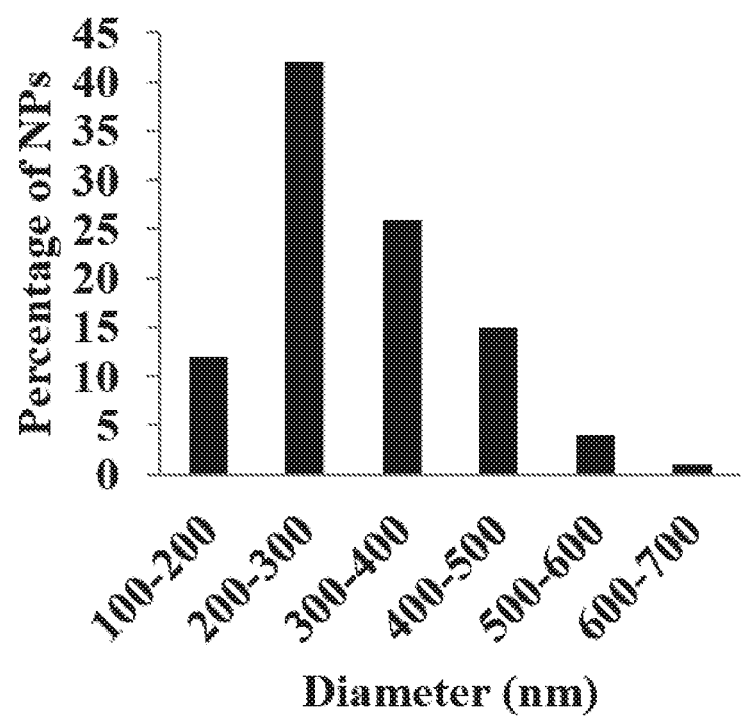
Figure 1C:
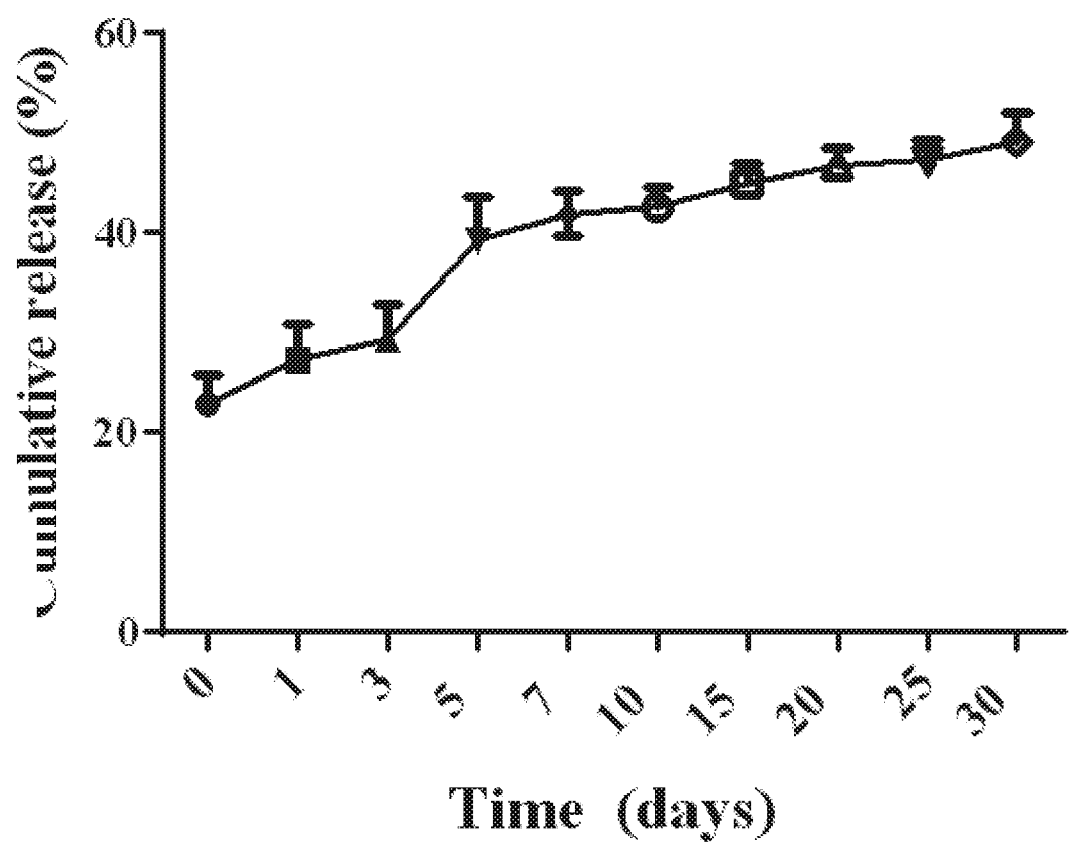

The encapsulation efficiency of KAg in PLGA-NPs was 57%. This result was comparable to previous results of PLGA encapsulation of peptides as well as inactivated PRRSV with 50-60% encapsulation efficiency (Hiremath J, et al. 2016. PLoS One 11:e0151922; Dwivedi V, et al. 2013. Vet Microbiol 166:47-58). Morphology of PLGA-KAg was determined by scattering electron microscope and size distribution was calculated by analyzing 200 NPs using the ImageJ software. PLGA-KAg were spherical in shape (FIG. 1A) with the mean diameter of 313 nm and standard deviation of 105 nm. Most of the NPs were in the size range of 200-300 nm diameter. For efficient uptake of NPs by APCs and M cells at mucosal surface, the ideal particle size is ≤500 nm (Foged C, et al. 2005. Int J Pharm 298:315-322; Gregory A E, et al. 2013. Front Cell Infect Microbiol 3:13), and approximately 95% PLGA-KAg particles were ≤500 nm (FIG. 1B). The charge of NPs was determined by a Quasi elastic light scattering experiment and found to be −18±0.56 mV. The particle size and charge were comparable to previous PLGA NPs (Binjawadagi B. et al. 2014. Int J Nanomedicine 9:679-694; Hiremath J, et al. 2016. PLoS One 11:e0151922; Dwivedi V, et al. 2013. Vet Microbiol 166: 47-58). During viral antigen encapsulation in NPs a fraction of the antigen is always associated on the surface of particles, which gets released immediately (≤30 min) after reconstitution in physiological buffers like PBS and it is called burst release (Rawat A, et al. 2008. J Control Release 128:224-232). There was a burst release of 22%, and after 24 hrs 27% of encapsulated cumulative quantity of KAg was released. Further, slow and sustained release of antigen was observed over a period of 4 week and the total cumulative release of KAg was approximately 50% after one month (FIG. 1C). This result was comparable to earlier PLGA-NPs preparations encapsulated with peptides and inactivated PRRSV (Binjawadagi B, et al. 2014. Int J Nanomedicine 9:679-694: Hiremath J, et al. 2016. PLoS One 11:e0151922).

Figure 1E:
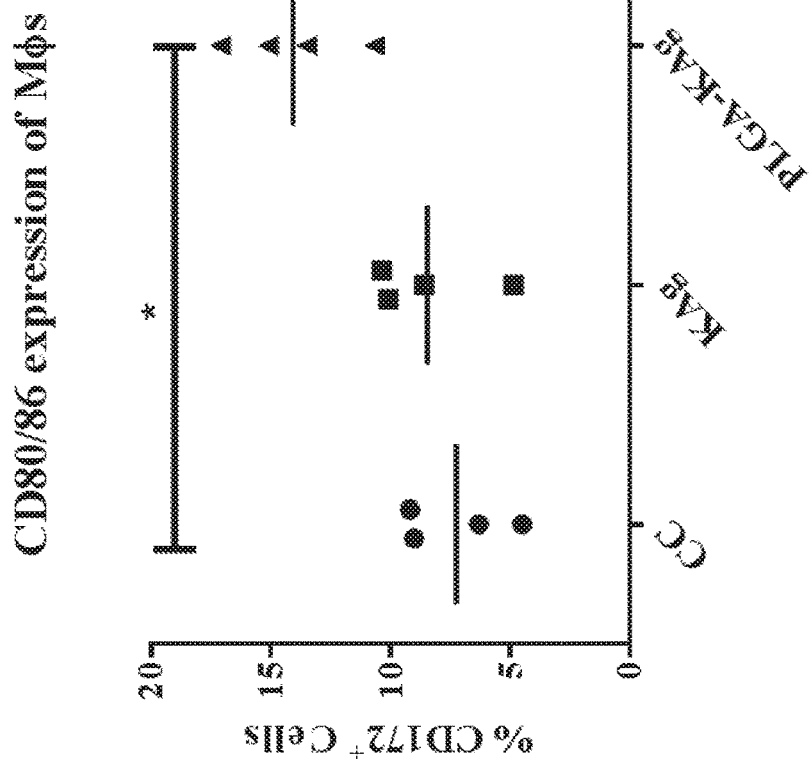
Figure 1D:
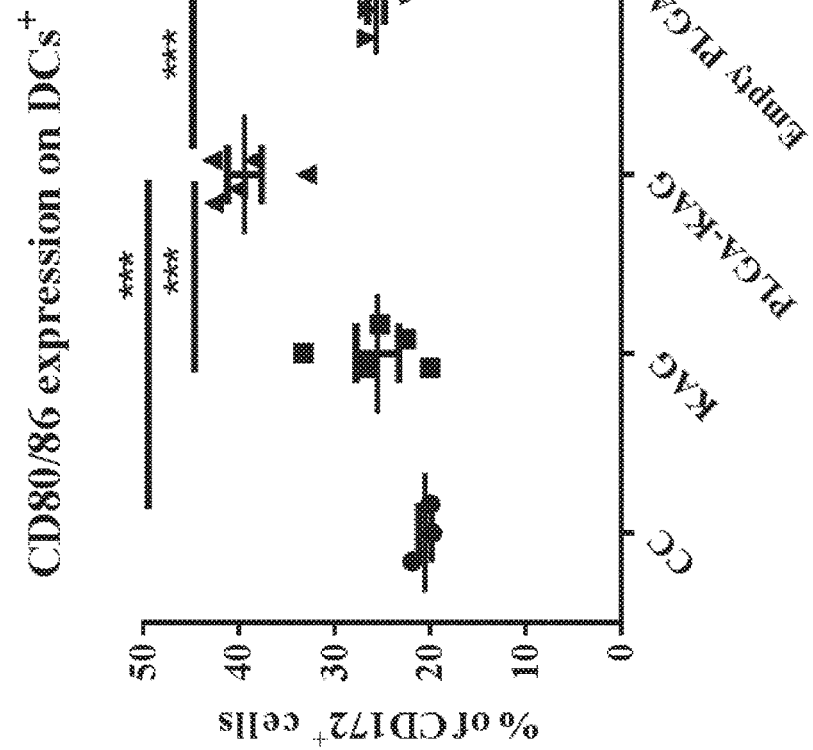

PLGA-KAg NPs induced maturation of antigen presenting cells in vitro. MΦs and DCs are the major APCs. Like in other species, porcine BAL cells contain >90% MΦs (Ganter M, Hensel A. 1997. Res Vet Sci 63:215-217), and hence BAL cells were used as a source of MΦs along with MoDCs to investigate the adjuvant properties of PLGA-KAg in vitro. BAL cells and MoDCs were treated with medium only, KAg (2 µg/ml) or PLGA-KAg (containing 2 µg/ml of KAg) and analyzed for the expression of APCs maturation marker, costimulatory molecule CD80/86. MoDCs were also treated with empty PLGA-NPs at the same w/v concentration present in the PLGA-KAg to determine the adjuvant role of PLGA-NPs alone. Results showed that in PLGA-KAg treated MoDCs expression of CD80/86 was significantly higher (40%) compared to medium control, KAg alone and empty PLGA-NPs treatment (<25%) (FIG. 1D). Similarly, in MΦs also expression of CD80/86 was significantly higher in PLGA-KAg treated compared to medium control. The percentage of CD80/86+ expression in PLGA-KAg treated MΦs (14%) was higher than KAg only treatment (8.5%) (FIG. 1E). This trend was similar when BAL cells and MoDCs were treated with higher concentration of the KAg (20 µg/ml). Furthermore, empty PLGA-NPs and KAg only also induced slightly increased CD80/86 expression in MoDCs (26%) compared to medium control (21%) (FIG. 1D). PLGA-NPs compared to PLGA-KAg particles had significantly higher adjuvant effects on treated MoDCs, suggesting the additive adjuvanticity of KAg when encapsulated in NPs.

PLGA-KAg NPs Vaccine Induced Antigen Specific Cellular Response in Pigs Pre-Challenge.

Figures 2A, 2B:
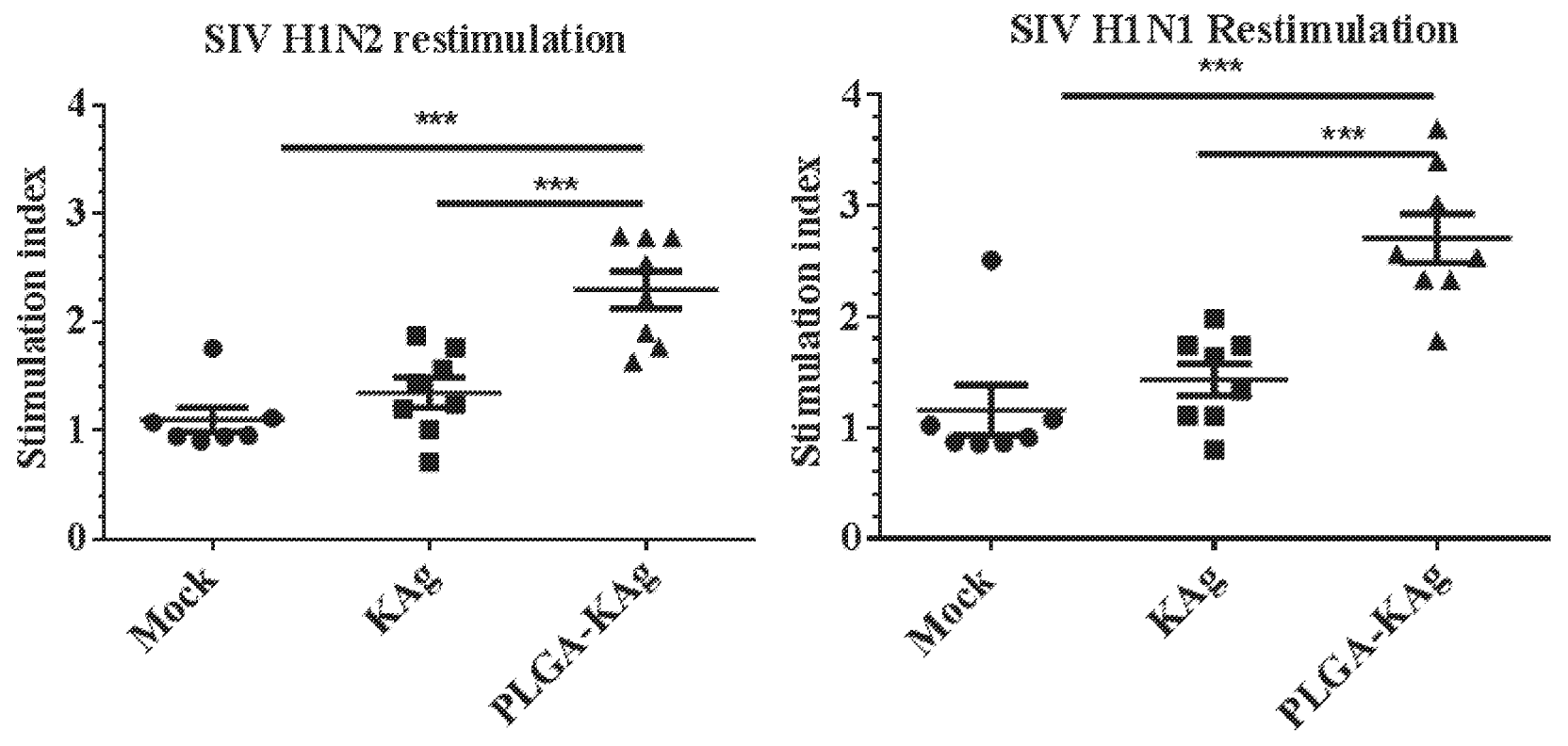
Figure 2D:
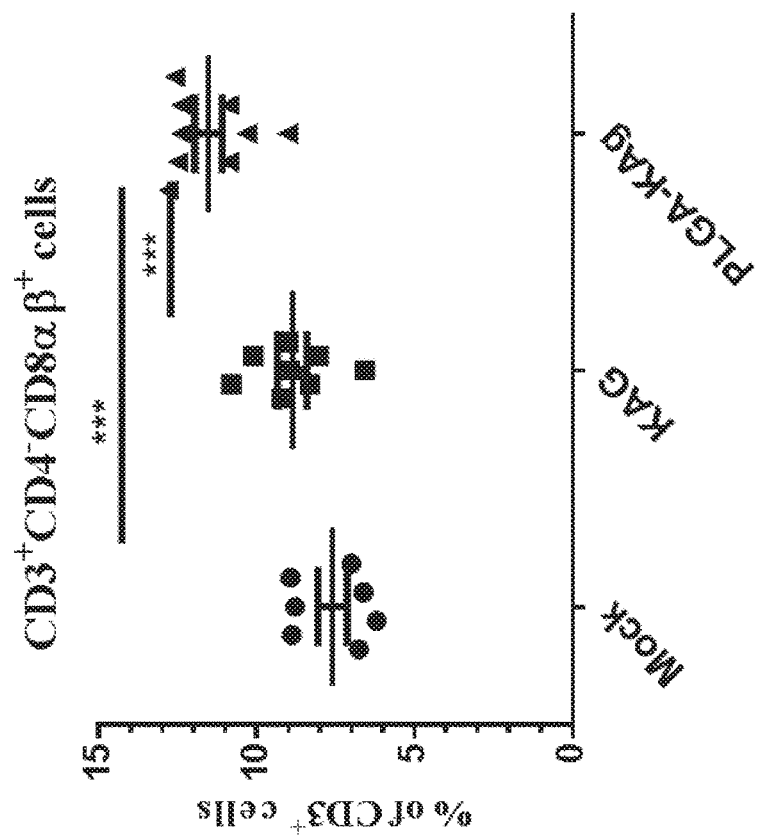
FIG. 2: Cellular and humoral immune responses in PLGA-KAg vaccinated pigs pre-challenge. Isolated PBMCs after prime-boost vaccination at DPV 35/DPC 0 were restimulated and specific lymphocyte proliferation was determined against (A) homologous vaccine virus (SwIV H1N2) and (B) heterologous challenge virus (SwIV H1N1). Frequencies of (C) CD3+CD4+CD8$\alpha$+cells; (D) CD3+CD4+CD8$\alpha\beta$+ cells; and (E) CD3+$\delta$+$\gamma\delta$ T cells in PBMCs were determined at DPC 0 by flow cytometry analysis. For humoral immune response evaluation, (F) HI titer in plasma and (G) IgG antibody response in plasma at 1:200 dilution were determined against the homologous vaccine virus (SwIV H1N2). Data were analyzed by one way ANOVA followed by Tukey's post-hoc test. Asterisk refers to statistical difference between two indicated pig groups (* refers $p<0.05$;  refers $p<0.01$; and * refers $p<0.001$).
Figure 2C:
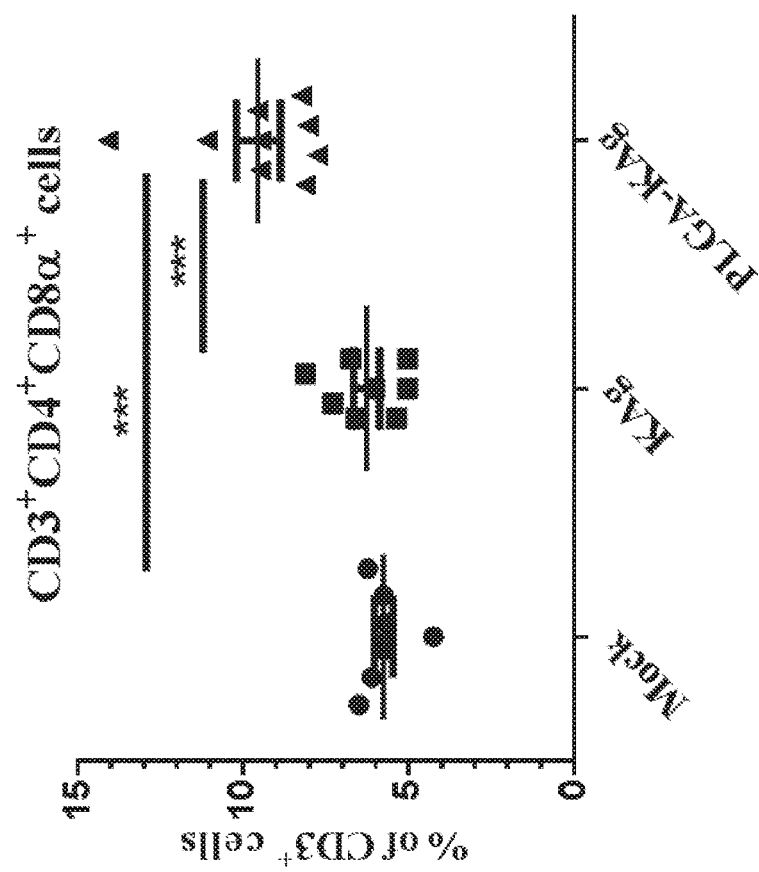
Figure 2F:
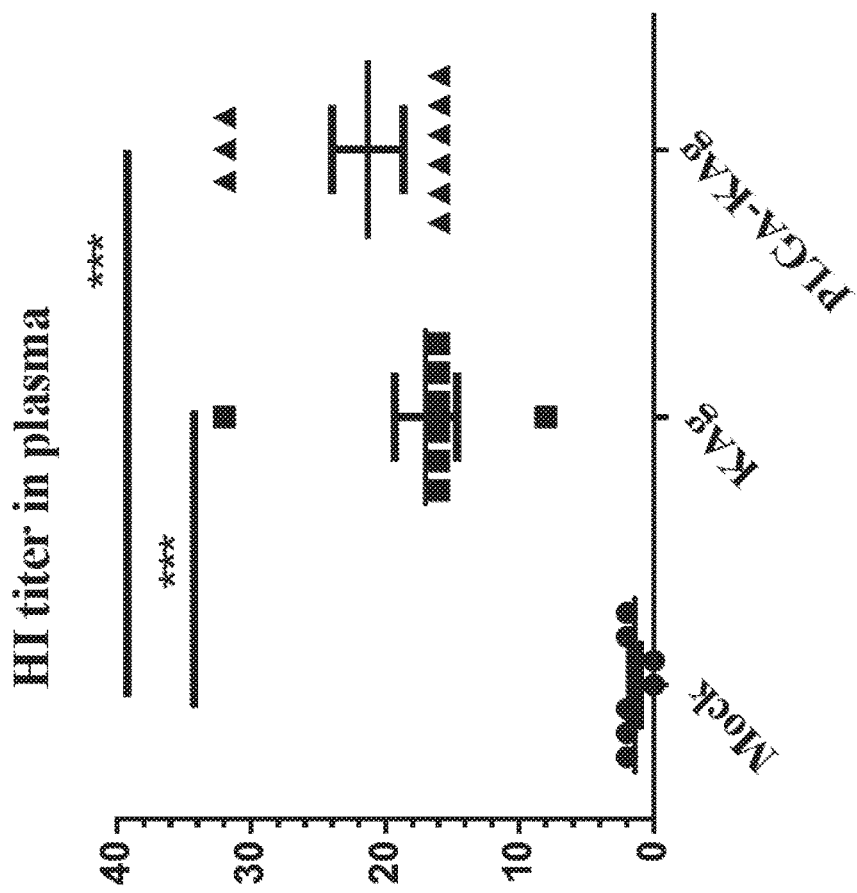
Figure 2E:
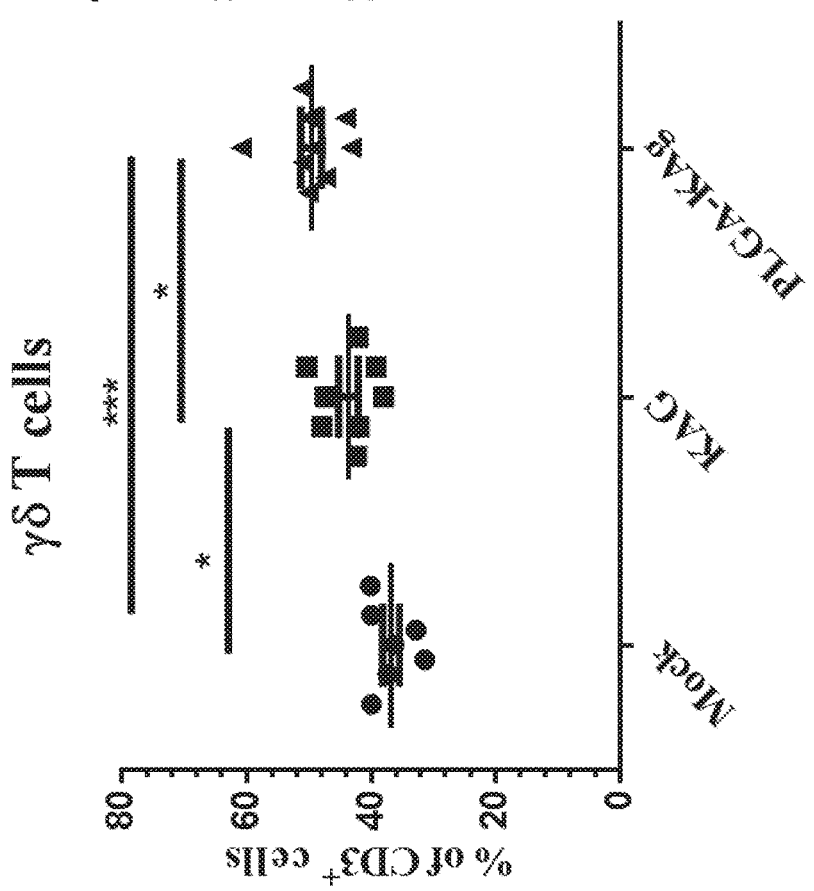

Stimulation index (SI) of PLGA-KAg vaccinated pigs was significantly higher compared to mock and KAg vaccinated animals stimulated with either the SwIV H1N2 (FIG. 2A) or H1N1 (FIG. 2B), indicating that PLGA-KAg vaccine recipient pigs had immune cells sensitized even against the heterologous SwIV. Flow cytometry analysis of PBMCs at DPV 35 (without any SwIV stimulation) demonstrated that PLGA-KAg vaccination induced generation of significantly higher frequency of $CD3^+CD4^+CD8\alpha^+$ T cells (FIG. 2C), which are called as activated/memory T helper cells in pigs (Zuckermann F A. 1999. Vet Immunol Immunopathol 72:55-66), and also cytotoxic T cells ($CD3^+CD4^+CD8\alpha\beta^+$) compared to KAg received pig group (FIG. 2D). There was also significantly increased frequency of γδ T cells in PLGA-KAg vaccinated pigs compared to KAg group (FIG. 2E).

Figure 2G:
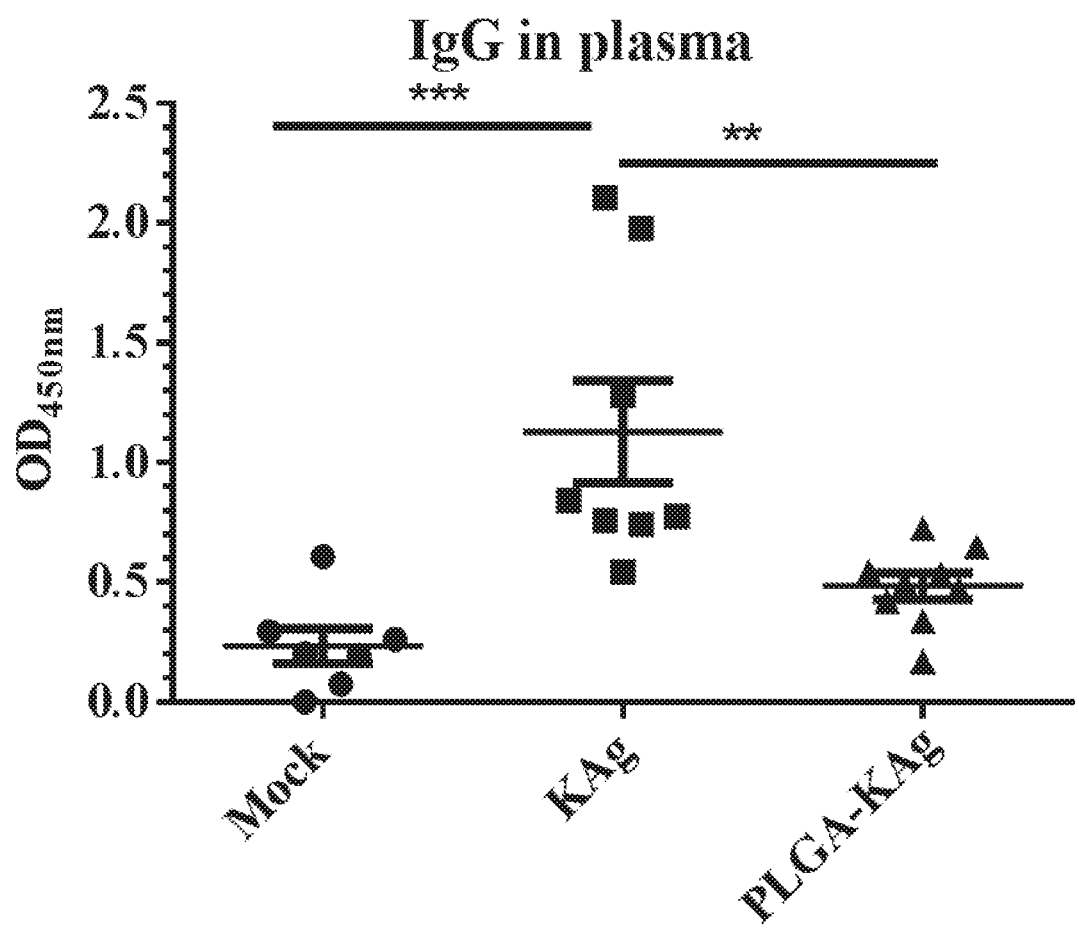

Significantly higher HI titer was observed both in KAg and PLGA-KAg vaccinated pig groups compared to mock group. However, no statistical difference was observed in HI titer between KAg and PLGA-KAg received groups (FIG. 2F). Interestingly, plasma IgG antibody response was significantly higher in KAg vaccinated pigs compared to PLGA-KAg recipients (FIG. 2G). There was no observable difference in IgA antibody titers in nasal swab samples collected at DPV 35/DPC 0 among different vaccine groups. Pre-challenge data demonstrated that PLGA encapsulation of inactivated SwIV delivered intranasally in pigs induced a skewed cell-mediated with moderate to weak humoral immune response.

PLGA-KAg NPs Vaccine Rescued Pigs from Clinical Flu Symptoms, Lung Pathology and Viral Load in the Lungs Post-Challenge.

Figure 3A:
FIG. 3: Intranasal route of PLGA-KAg vaccination reduced the clinical flu caused by a heterologous virus challenge in pigs. (A) Pigs were vaccinated with KAg or PLGA-KAg intranasally as a mist using a multidose delivery device. (B) Rectal body temperature of pigs was recorded daily post-challenge.
Figure 3B:
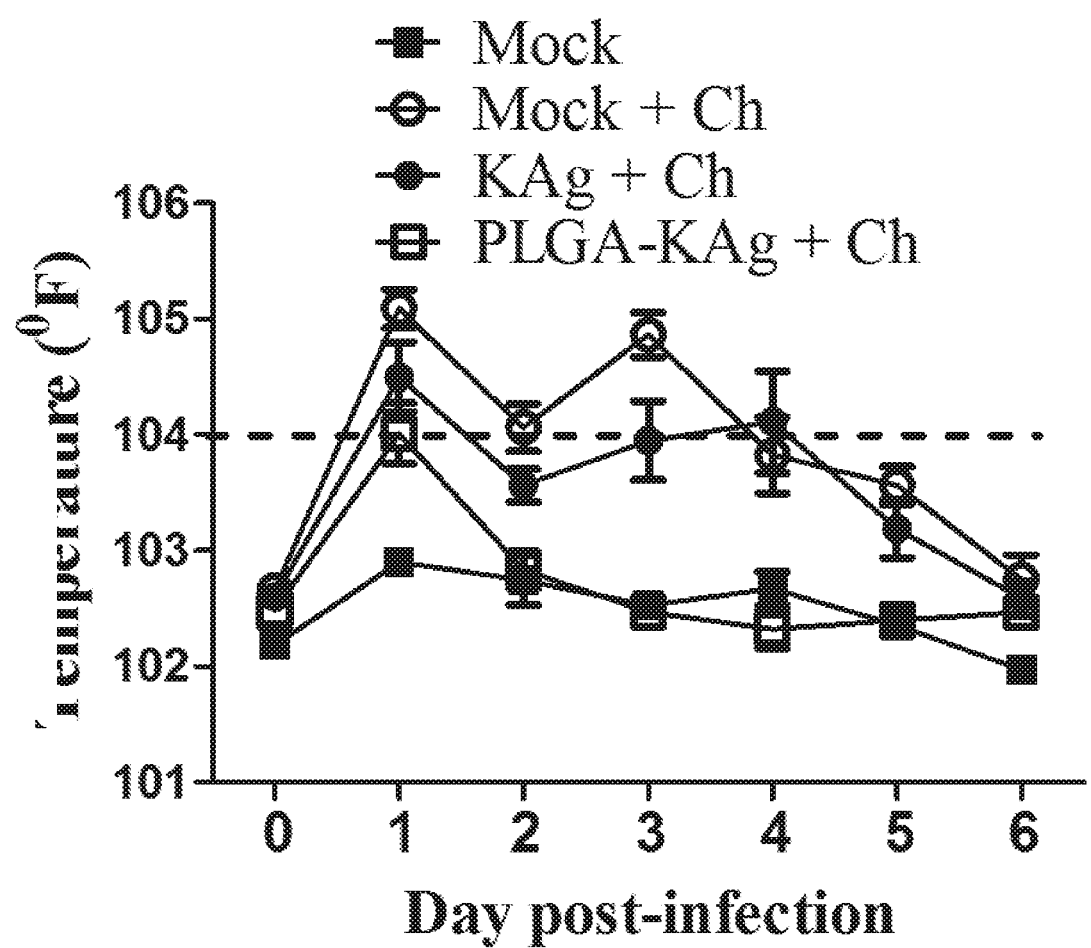

Pigs were vaccinated intranasally using the multidose aerosoal device which provides fine mist particles (FIG. 3A). In SwIV H1N1 challenged, mock and KAg vaccinated pigs there was fever with the mean rectal temperature until DPC 4 remained >104° F., and also most of those pigs were anorexic and lethargic during those four days post-challenge (FIG. 3B). While PLGA-KAg vaccinated pigs had fever only until DPC 1 (FIG. 3B) with mild flu symptoms, and from DPC 2 onwards they were apparently normal and comparable to mock pigs.

Figure 4A:
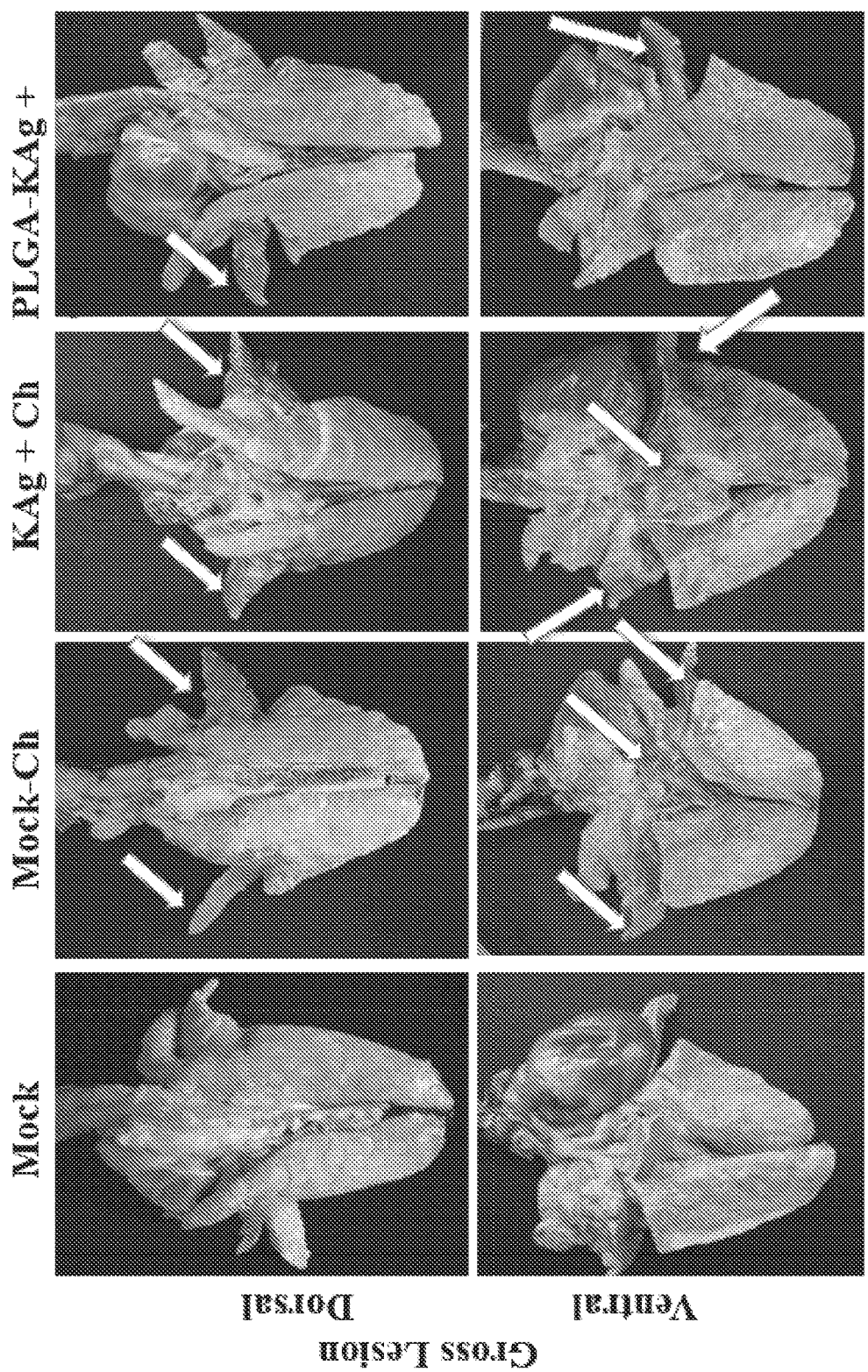
FIG. 4. Reduced lung lesions in pigs vaccinated with PLGA-KAg and virulent virus challenged. A representative lung picture of every experimental pig groups is shown: (A) Gross lung lesions of consolidation are indicated by arrows; (B) microscopic lung sections stained by H&E; and (C) immunohistochemistry analysis of lung sections for SwIV antigens.

On the day of necropsy (DPC 6) lungs were examined and scored for percentage consolidation due to influenza infection. The gross lung lesion scores in PLGA-KAg vaccinated pigs (mean=12.1) was lower than KAg group (mean=20.8) and significantly lower than mock-infected animals (mean=23.9) (Table 2). The representative lung pictures showing gross lung lesions are shown (FIG. 4A). Microscopic lung lesions showed lower percentage of inflammatory cell infiltration around the bronchioles and bronchial epithelium of PLGA-KAg vaccinated pigs, suggesting the vaccine induced protection in the lungs of heterologous SwIV challenged pigs (FIG. 4B; Table 2).

The antigenic mass in PLGA-KAg vaccinated and virus challenged pigs was significantly lower than mock as well as KAg vaccinated and virus challenged animals (Table 2). The IHC scores and H&E results revealed that the lungs of PLGA-KAg vaccinated pigs were least affected by the virulent heterologous challenge virus, and they were comparable to mock uninfected pigs at DPC 6 in terms of influenza antigenic mass. The representative IHC pictures from each of respective pig groups are shown (FIG. 4C).

The infectious SwIV H1N1 virus titer in the BAL fluid at DPC 6 was determined, and all the mock vaccinated and virus challenged pigs were found positive for virus (8/8), while 5 of 8 KAg and only 2 of 9 PLGA-KAg vaccinated pigs were positive for the SwIV H1N1. Though both KAg and PLGA-KAg significantly reduced the virus titer in the BAL fluid compared to mock-infected pigs, PLGA encapsulation of KAg led to 2 log more reduction in the infectious lung virus titer compared to KAg vaccination in pigs. Overall, in PLGA-KAg vaccinated pigs a total of 5 log reduction in virus titer was observed compared to mock-infected animals (Table 2). Further, virus shedding was also tested in nasal swabs at DPC 4 and 6, but surprisingly unlike in the BAL fluid, nasal viral shedding at DPC 4 was comparable in all the vaccinated and mock-infected pig groups; and by DPC 6 it was equally reduced across all the groups. Overall, there was no difference in the nasal virus shedding between the KAg and PLGA-KAg vaccine recipient pigs (Table 2). Data suggested that intranasal delivery of PLGA encapsulated SwIV KAg provided clinical protection against a heterologous virus challenge and reduced the lung pathology and replicating infectious virus load in the lungs.

PLGA-KAg Vaccination Induced Enhanced IFNγ Secretion and Activated Recall T Cell Response in Virus Challenged Pigs.

Figure 5:
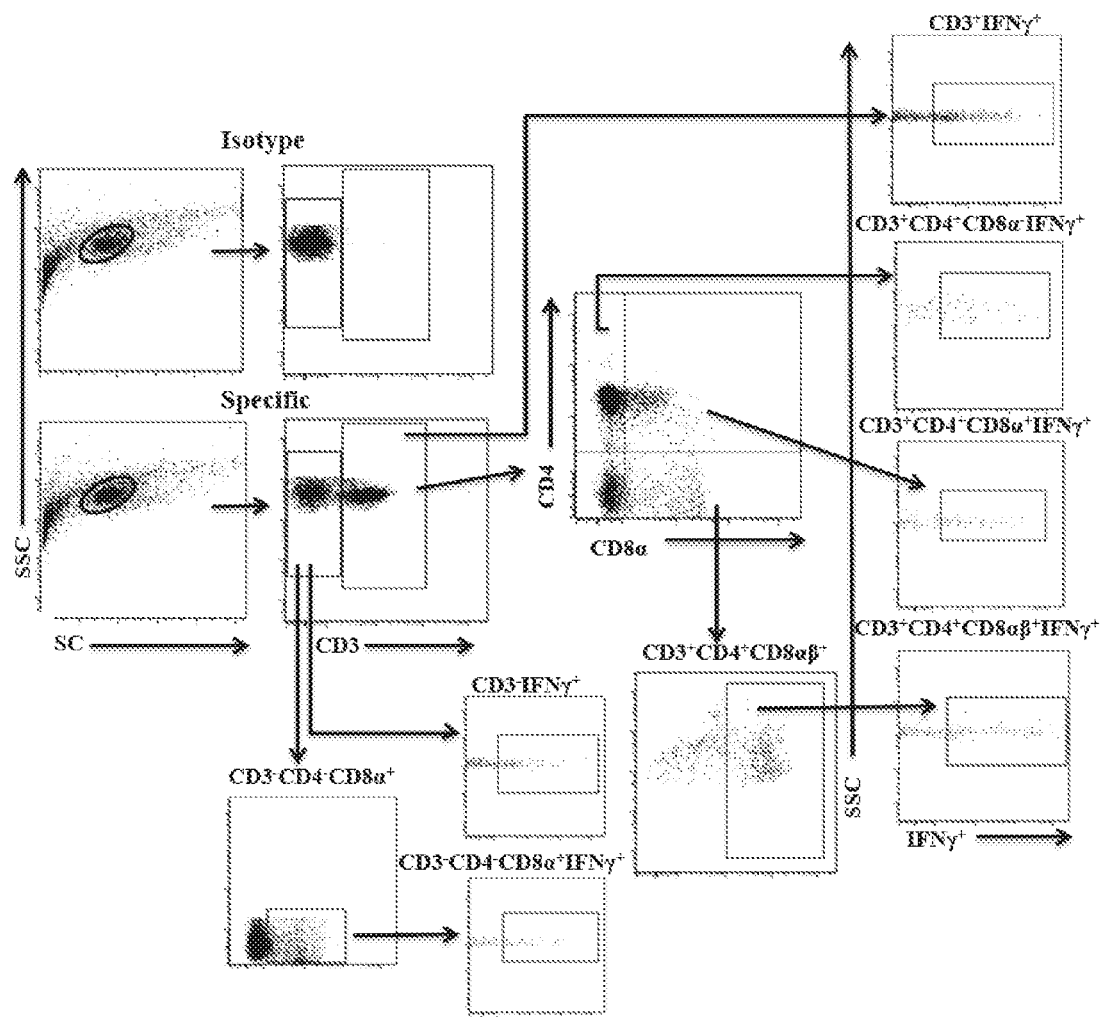
FIG. 5. A representative flow cytometry plots showing the gatting pattern of pig lymphocytes. PBMCs isolated at DPC 6 from PLGA-KAg vaccinated and virus challenged pigs were restimuatled with SwIV H1N1 and treated with Golgiplug/block, and immunostained using pig specific lymphocyte surface markers followed by intracellular IFNγ, and estimated the frequency of activated (IFNγ+) lymphcocyte subpopulations. Gating pattern of isotype and lymphocyte specific markers stained with CD3ε, CD4α, CD8α, CD8β and IFNγ to identify the frequency of CD3-IFNγ+, CD3-CD4-CD8α+IFNγ+, CD3+IFNγ+, CD3+CD4+CD8α-IFNγ+, CD3+CD4+CD8α+IFNγ+ and CD3+CD4-CD8αβ+IFNγ+ cells are shown.

At pre-challenge DPC 0 augmented cellular immune response in PLGA-KAg vaccinated pigs in PBMCs was detected (FIG. 2), therefore a similar analysis was performed post-challenge at DPC 6 in pig groups. To reveal the recall cellular response, PBMCs were stimulated ex vivo with either the vaccine (H1N2) or challenge (H1N1) SwIV and analyzed for the activated (IFNγ$^+$) T lymphocyte subsets. A representative graph showing gating pattern followed for analysis of different T cell subsets in pigs by flow cytometry is shown (FIG. 5).

Figures 6A, 6B:
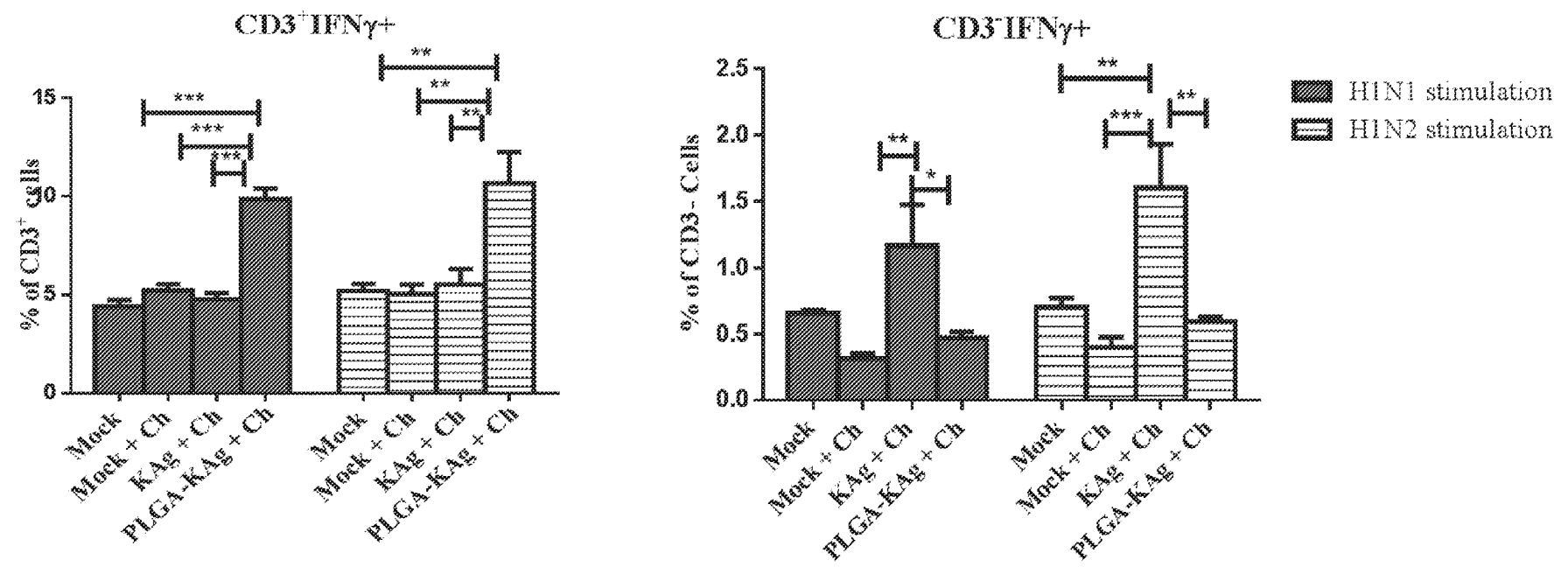
Figures 6C, 6D:
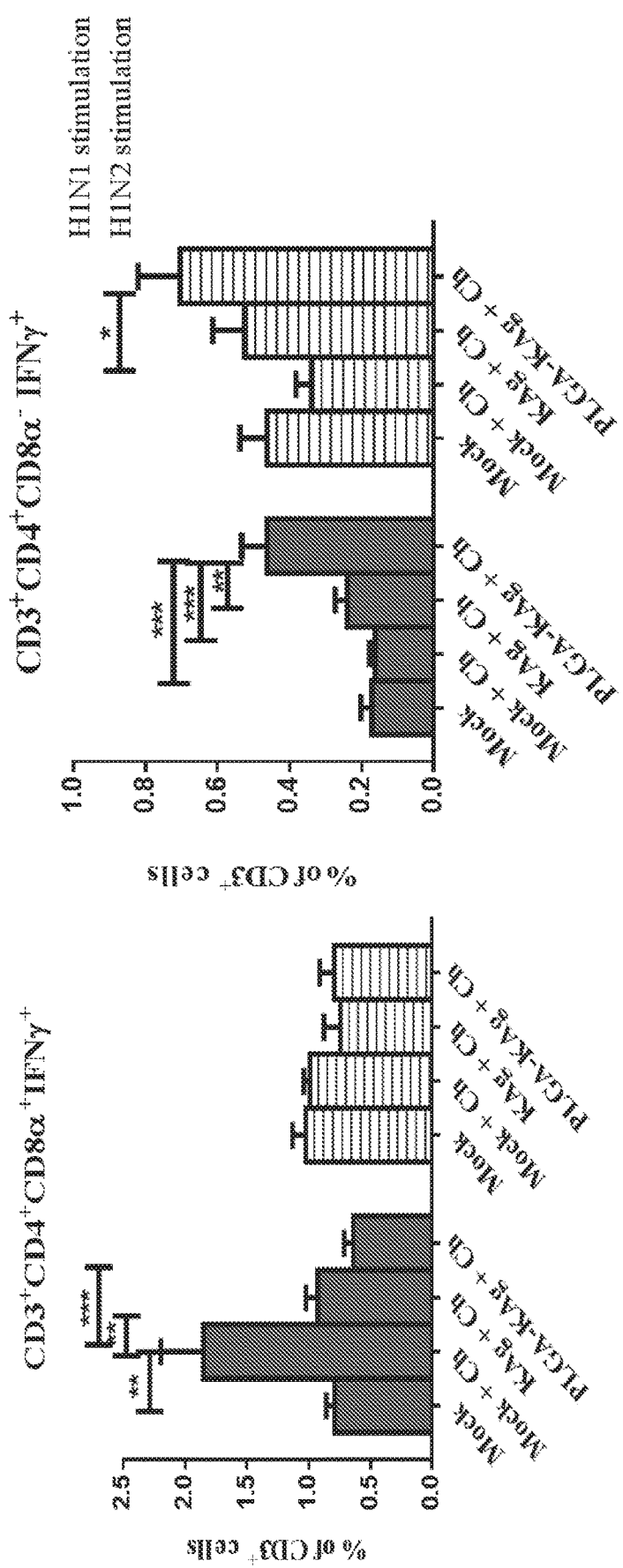
FIG. 6. Lymphocytes recall response in PLGA-KAg vaccinated and virus challenged pigs were significantly augmented. On the day of necropsy (DPC 6) isolated PBMCs were restimulated with vaccine or challenge virus and the frequency of activated (IFNγ+) lymphocytes were determined by flow cytometry. Average frequency of lymphocytes: (A) CD3+IFNγ+; (B) CD3-IFNγ+; (C) CD3+CD4+CD8α+IFNγ+; (D) CD3+CD4+CD8α-IFNγ+; (E) CD3+CD4-CD8αβ+IFNγ+; and (F) CD3-CD4-CD8α+IFNγ+ from all the experimental pig groups were quantified. Each bar indicates the average frequency of indicated lymphcocyte subset of 7 or 9 pigs±SEM. Data were analyzed by one way ANOVA followed by Tukey's post-hoc test. Asterisk refers to statistical significant difference between the two indicated pig groups (*$p<0.05$; $p<0.01$; and *$p<0.001$).
Figure 6E:
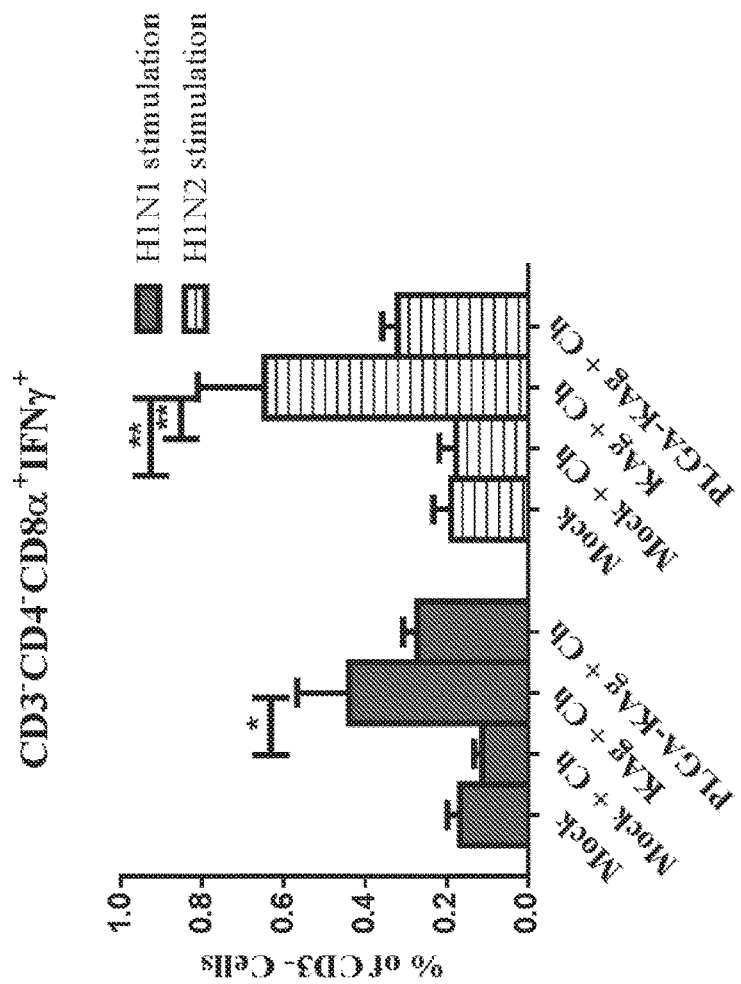
Figure 6F:
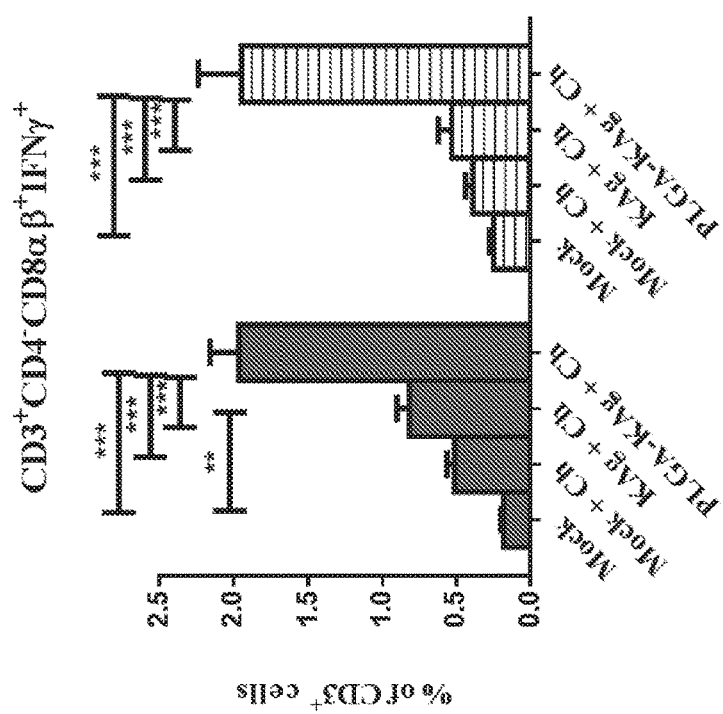

Total IFNγ producing T cells (CD3$^+$) were significantly higher in PLGA-KAg received pig group compared to KAg received animals stimulated with both vaccine and challenge viruses (FIG. 6A). CD3$^-$IFNγ$^+$ cells were significantly higher in KAg than PLGA-KAg vaccinated pig groups, irrespective of virus re-stimulation conditions (FIG. 6B). CD3$^+$CD4$^+$CD8α$^+$IFNγ$^+$ (activated T-helper/memory) cells were significantly higher in mock-challenge pig group in response to ex vivo stimulation with challenge virus, but not with vaccine virus, suggesting the activation of memory cells in pigs (FIG. 6C). CD3$^+$CD4$^+$CD8α$^-$IFNγ$^+$ (activated T-helper) cells were significantly higher in PLGA-KAg vaccinated pig group compared to both mock-challenge and KAg received groups cells stimulated with challenge virus, but significantly enhanced compared to mock-challenge group on stimulation with vaccine virus (FIG. 6D). IFNγ producing CD3$^+$CD4$^-$CD8αβ$^+$IFNγ$^+$ (activated cytotoxic T) cells were significantly augmented in PLGA-KAg vaccinated pig group compared to both mock-challenge and KAg vaccinated animals stimulated with both vaccine and challenge viruses (FIG. 6E). Consistent with increased CD3-IFNγ cell subset response observed in KAg vaccinated pig group, IFNγ producing NK cell subsets (CD3$^-$CD4$^-$CD8α$^+$IFNγ$^+$) were also significantly higher compared to mock challenged animals (FIG. 6F).

Figure 7A:
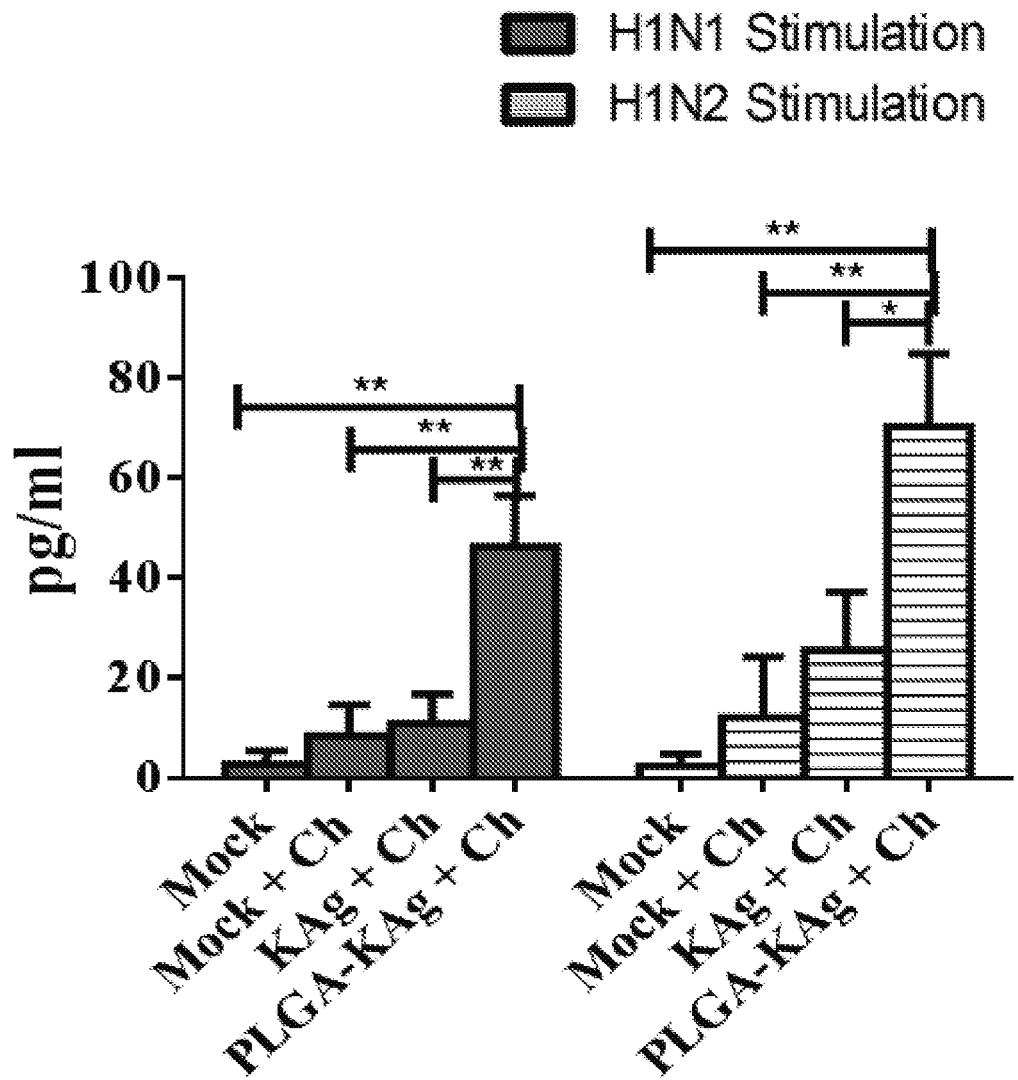
FIG. 7. Enhanced IFNγ secretion and recall T cell response in PLGA-KAg vaccinated and virus challenged pigs. PBMCs isolated at DPC 6 were restimulated with vaccine or challenge virus for 3 days. (A) Cell culture supernatant was harvested and determined the levels of secreted IFNγ by ELISA. The recall cellular response in PBMCs of only PLGA-KAg vaccinated pigs restimulated (SwIV H1N1 or H1N2) or unstimulated (cell control, CC) are shown in terms of frequencies of lymphocytes: (B) CD3+IFNγ+; (C) CD3+CD4-CD8αβ+IFNγ+; and (D) secreted IFNγ in cell culture supernatant. The percent cells shown above the dotted line represents specific recall T cell response over no stimulation. Each bar indicates the average frequency of indicated lymphcocyte subset of 7 or 9 pigs±SEM. Data were analyzed by one way ANOVA followed by Tukey's post-hoc test. Asterisk refers to statistical significant difference between the two indicated pig groups (*$p<0.05$; **$p<0.01$).
Figures 7B, 7C, 7D:
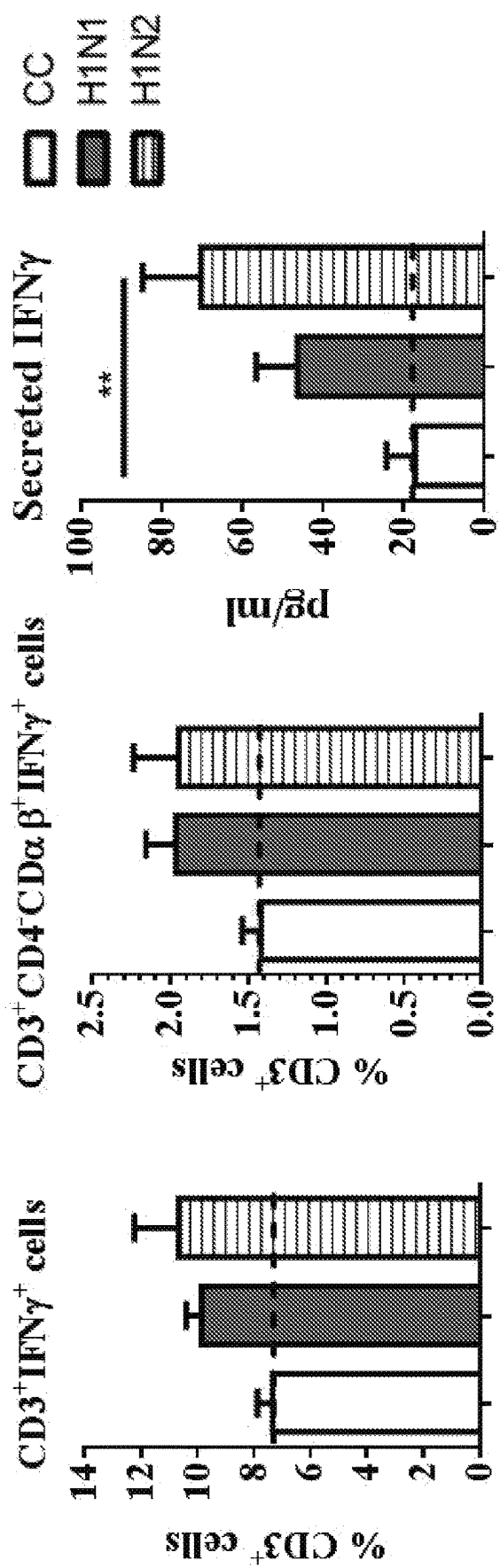

Consistent with the flow cytometry data, IFNγ secretion by re-stimulated PBMCs was also significantly higher in PLGA-KAg vaccinated and virus challenged pigs compared to both mock-challenge and KAg vaccinated animals (FIG. 7A). Since PLGA-KAg had induced very strong T cell response, antigen specific recall response exclusively in PLGA-KAg vaccinated pigs was further determined by comparing IFNγ$^+$ cell frequencies in PBMCs unstimulated (cell control, CC) or stimulated with SwIV H1N1 or H1N2. Results indicated an increased (but not significant) frequencies of both CD3$^+$IFNγ$^+$ and CD3$^+$CD4$^-$CD8αβ$^+$IFNγ$^+$ cells stimulated with both the SwIV (FIGS. 7B and C). Further, IFNγ secretion into the cell culture supernatant was significantly higher in H1N2 stimulated PBMCs of PLGA-KAg vaccinated pig group compared to unstimulated cells (FIG. 7D), indicating the presence of antigen specific recall Th1 response. To note that due to analysis of recall T cell response just after 6 days post-challenge in PLGA-KAg vaccinated pigs, high percent of effector T cells were detected (CC stimulation) (FIGS. 7B and C). Thus, to exclusively understand SwIV specific memory T cell response in PLGA-KAg vaccinated pigs, a similar analysis at least 3 to 6 months post-vaccination is needed. Overall, lymphocyte response analysis data both at pre- and post-challenge in PLGA-KAg vaccinated pigs suggested induction of a strong cellular immune response.

KAg Compared to PLGA-KAg Vaccination Induced Higher IgA and IgG Responses, but HI and Virus Neutralization Titers were Comparable.

Figure 8B:
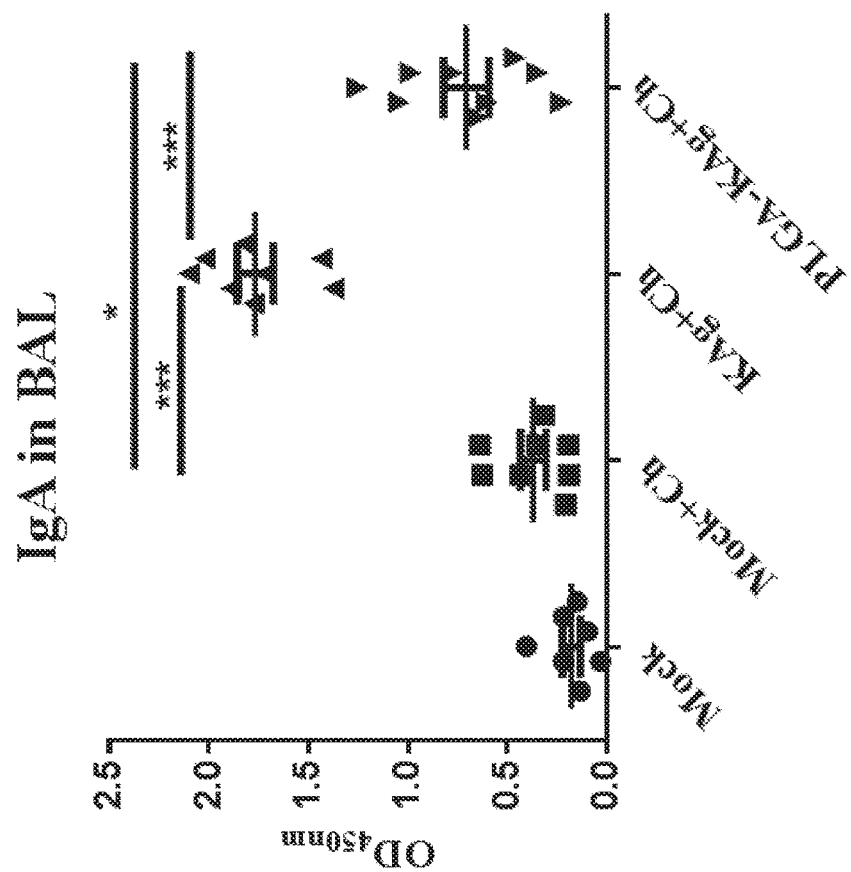
FIG. 8. Humoral immune response in vaccinated and virus challenged pigs. IgA antibody response against the challenge SwIV H1N1 in pigs in (A) undiluted nasal swab; and 1:200 diluted (B) BAL fluid and (C) lung lysate samples. IgG response against SwIV H1N1 in 1:200 diluted (D) plasma and (E) BAL fluid samples. HI titer in (F) BAL fluid and (G) plasma, and (H) VN titer in BAL fluid samples. Data were analyzed by one way ANOVA followed by Tukey's post-hoc test. Asterisk refers to statistical significant difference between the two indicated pig groups (*$p<0.05$; ***$p<0.001$).
Figure 8A:
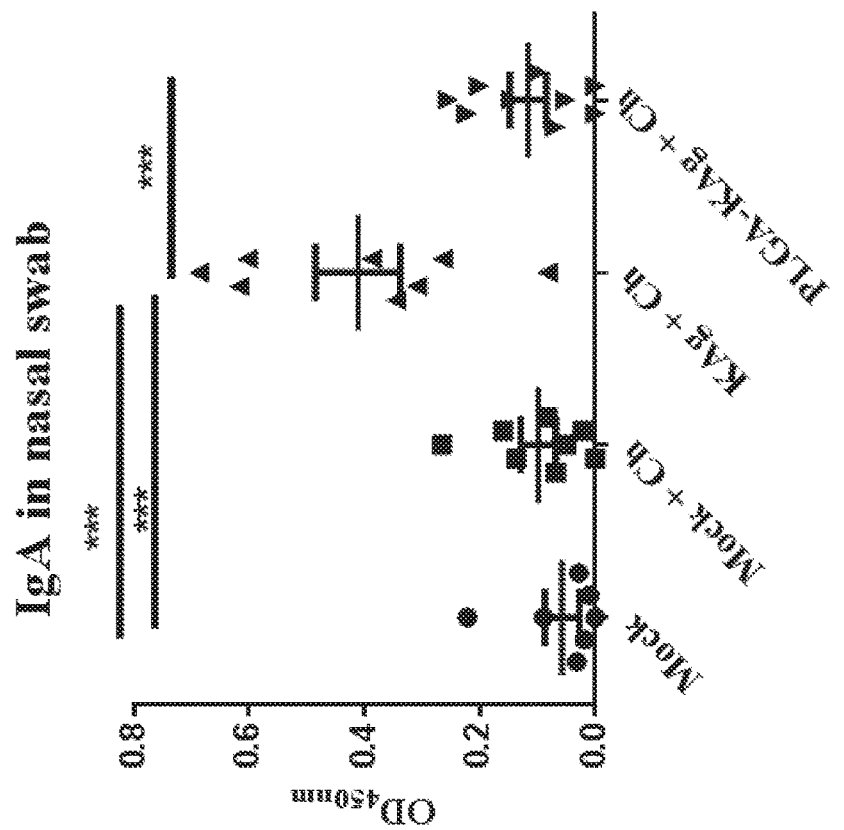
Figure 8D:
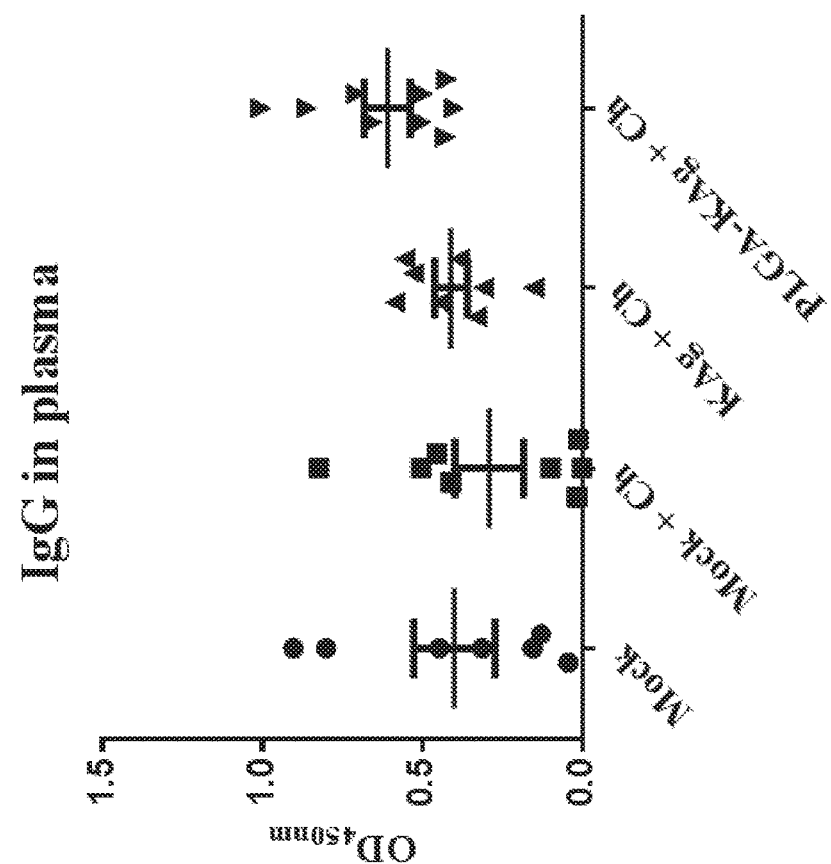
Figure 8C:
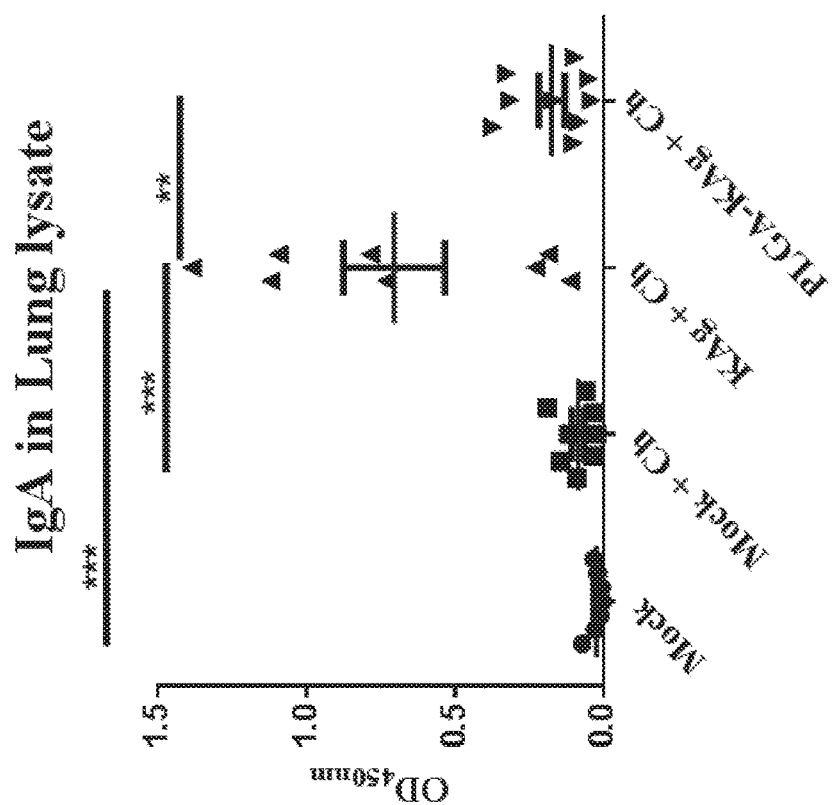
Figure 8F:
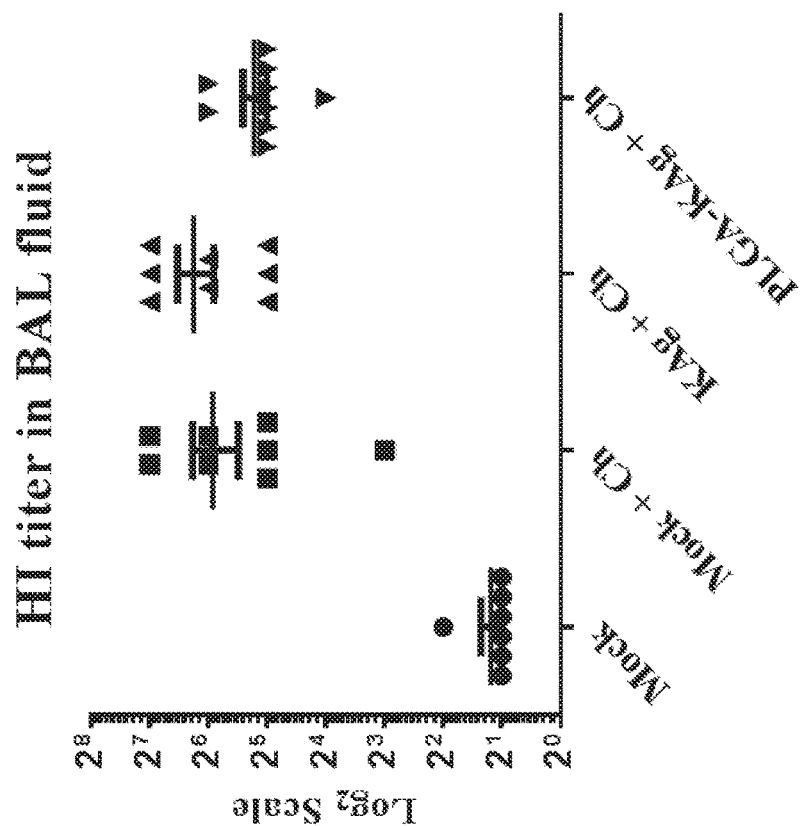
Figure 8E:
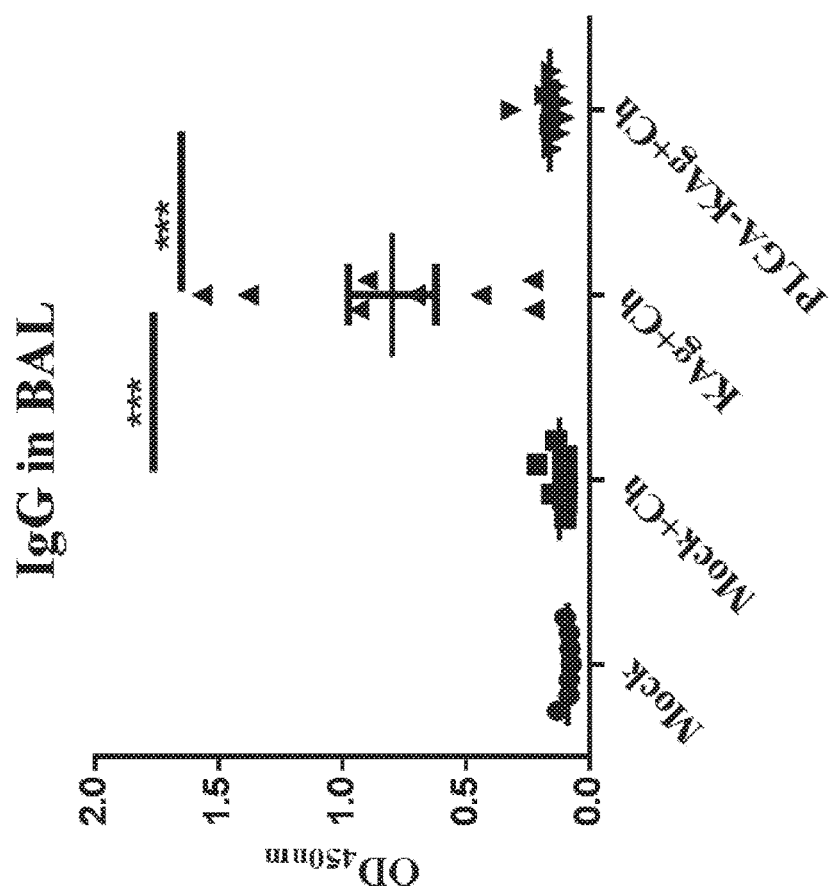
Figure 8H:
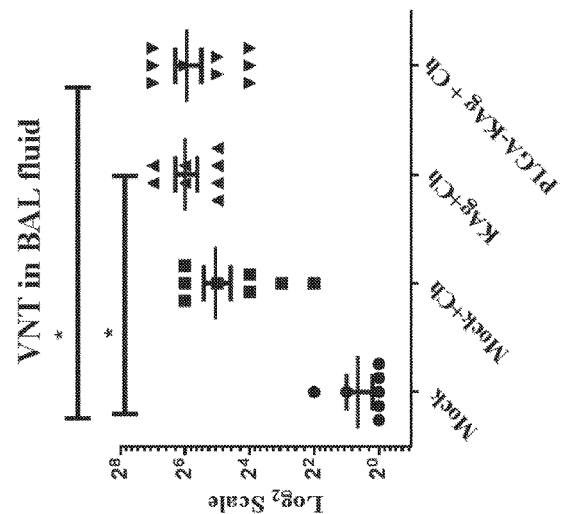
Figure 8G:
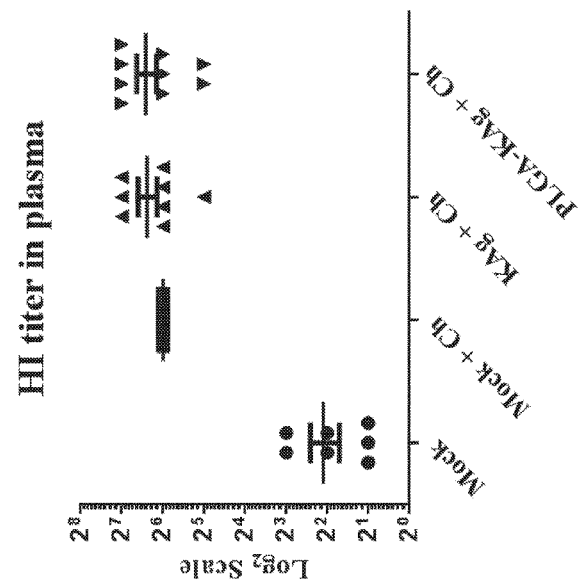

Intranasal delivery of vaccine is thought to induce strong local mucosal immunity. Therefore, IgA response was determined in nasal swab, BAL fluid and lung lysate samples, demonstrating significantly higher response against SwIV H1N1 in KAg compared to PLGA-KAg vaccinated and virus challenged pigs (FIG. 8A-C). Specific IgG antibody levels against SwIV H1N1 was also checked. No difference in the plasma among all the experimental pig groups was detected (FIG. 8D), but the levels were significantly higher in BAL fluid of KAg vaccinated pigs (FIG. 8D-E). IgA and IgG antibody response against vaccine virus (SwIV H1N2) also had a similar higher trend in KAg rather than PLGA-KAg vaccinated pigs. There was an absence of statistical difference in HI titer against SwIV H1N1 in the BAL fluid and plasma between KAg and PLGA-KAg vaccinated pig groups (FIG. 8F-G). Similarly, there was no difference in HI titer against SwIV H1N2 in plasma, but HI titer in BAL fluid against SwIV H1N2 was significantly higher in PLGA-KAg compared to KAg vaccinated pig groups. Surprisingly, irrespective of significantly higher IgG and IgA antibody response detected in KAg vaccinated pigs, the virus neutralization titers were comparable to that of PLGA-KAg vaccinated animals (FIG. 8H). Overall, cellular and humoral immune response data suggested that intranasal vaccination with both the KAg and PLGA-KAg failed to induce strong HI and virus neutralizing antibody responses locally at the lungs as well as systemically in blood of pigs. However, PLGA encapsulation of SwIV KAg elicited strong cross-protective cell-mediated immunity.

Discussion

PLGA polymer is extensively used in drug and vaccine delivery studies due to its non-toxic, biodegradable and biocompatible properties (Danhier F, et al. 2012. J Control Release 161:505-522). PLGA based candidate viral vaccines delivered intranally in rodent models in the absence of any adjuvant have shown great promise against hepatitis B, equine encephalitis, influenza and parainfluenza by inducing strong cellular and humoral immune responses (Thomas C, et al. 2011. Mol Pharm 8:405-415; Greenway T E, et al. 1998. Vaccine 16:1314-1323; Shephard M J, et al. 2003. Res Vet Sci 74:187-190; Yassine H M, et al. 2015. Nat Med 21:1065-1070; Liu Q, et al. J Med Virol 87:1807-1815; Singh M, et al. 2001. J Control Release 70:267-276). In dairy calves immunized intranasally with PLGA encapsulated bovine parainfluenza virus, enhanced virus specific antibody response was observed (Mansoor F, et al. 2015. BMC Veterinary Research 11:1-11). Studies in pigs indicated that intranasal delivery of PLGA-NPs based inactivated PRRSV induced enhanced cross-protective response only when coadministered with a potent adjuvant, supported with strong cellular and humoral immune responses (Binjawadagi B, et al. 2014. Int J Nanomedicine 9:679-694; Dwivedi V. et al. 2012. PLoS One 7:e51794; Binjawadagi B, et al. 2014. Int J Nanomedicine 9:1519-1535). In pigs vaccinated intranasally with PLGA-NPs encapsulated conserved IAV T and B cell peptides cocktail, peptide specific cellular immune response was upregulated, but the humoral immune response was weak; still the pigs did not suffer from clinical flu and replicating challenge virus in the lungs was cleared at DPC 7 (Hiremath J, et al. 2016. PLoS One 11:e0151922). In this study, the goal was to improve virus specific mucosal and systemic humoral response and to demonstrate cross-protective efficacy of PLGA-NPs containing inactivated SwIV, which likely provides greater number of potential B cell epitopes compared to selected few peptides to the immune system of pigs.

For prevention of transmission and efficient protection against influenza viruses which infect respiratory tract epithelial cells, induction of adequate mucosal antibody response is critical, and vaccine delivery through nostrils have that potential (Zaman M, et al. 2013. Methods 60:226-231; Almeida A J, et al. 1996. J Drug Target 3:455-467). In the disclosed study, specific HI titer was increased in PLGA-KAg vaccinated pigs against the vaccine virus, but not against the challenge heterologous virus. Interestingly, plasma IgG and BAL fluid IgA and IgG responses were significantly higher in KAg compared to PLGA-KAg vaccinated pigs at both pre- and post-challenge, but virus neutralization titer against the challenge virus in BAL fluid was comparable in KAg and PLGA-KAg vaccinated pigs. Clearance of replicating virus in 40% of pig lungs in KAg vaccinated compared to mock-infected pigs appears to be contributed by antibodies and increased innate NK cells, but the clinical disease and lung pathology was not reduced. Therefore, induction of strong cell-mediated immune response in inactivated SwIV vaccinated pigs is essential to limit the severity of influenza in pigs. Hence innovative vaccination strategies should explore T cell immunity to provide broad protective response (Moss P. 2003. Developments in biologicals 115:31-37; La Gruta N L, et al. 2014. Trends in Immunology 35:396-402). Activated lymphocytes produce IFN-$\gamma$, which play a significant role in influenza viral clearance (Hiremath J, et al. 2016. PLoS One 11:e0151922; Bot A, et al. 1998. Journal of Virology 72:6637-6645). PLGA-KAg induced less of IgA and IgG antibody response than KAg vaccination at mucosal and systemic sites, but still the HI and VN titers were comparable.

In summary, intranasal delivery of PLGA based inactivated SwIV vaccine induced strong cellular immune response, rescued pigs from clinical disease, reduced the lung pathology and heterologous challenge viral load in the lungs. Further, though the levels of antibody response elicited by PLGA-KAg was much higher than NPs entrapped H1N1 peptides vaccination in pigs (Hiremath J, et al. 2016. PLoS One 11:e0151922).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

TABLE 1

Experimental design showing assignments of pigs in each group

| Experimental groups | Pig Nos | Vaccine formulations | | |
|---|---|---|---|---|
| | | First vaccination (DPV 0/DPC −35) | Second vaccination (DPV 21/DPC −14) | Day of Challenge (DPV 35/DPC 0) |
| Mock | 7 | Mock inoculum | Mock inoculum | Mock inoculum |
| Mock + Chal. | 8 | Mock inoculum | Mock inoculum | SwIV OH7 (H1N1) |
| KAg + Chal. | 8 | Inactivated SwIV OH10 (H1N2) | Inactivated SwIV OH10 (H1N2) | SwIV OH7 (H1N1) |
| PLGA-KAg + Chal. | 9 | PLGA encapsulated inactivated SwIV OH10 (H1N2) | PLGA encapsulated inactivated SwIV OH10 (H1N2) | SwIV OH7 (H1N1) |

TABLE 2

Summary of pathological lung lesions scores and challenge virus titers[a]

| Treatment group | Gross lung lesion score | H&E score[b] | IHC score[b] | Virus titer[c] BAL fluid (DPC 6) | Nasal Swab DPC 4 | Nasal Swab DPC 6 |
|---|---|---|---|---|---|---|
| Mock | 0.0 ± 0.0 C (0/7) | 0.1 ± 0.0 A (6/7) | 0.1 ± 0.1 A (1/7) | 0.0 ± 0.0 A (0/7) | 0.0 ± 0.0 A (0/7) | 0.0 ± 0.0 A (0/7) |
| Mock + Chal. | 23.9 ± 3.1 B (8/8) | 1.5 ± 0.2 B (8/8) | 2.2 ± 0.4 B (8/8) | 5.3 ± 0.3 B (8/8) | 5.1 ± 0.1 B (8/8) | 2.3 ± 0.6 B (8/8) |
| KAg + Chal. | 20.8 ± 3.7 AB (8/8) | 1.3 ± 0.1 B (8/8) | 1.3 + 0.3 B (7/8) | 2.4 ± 0.7 C (5/8) | 5.0 ± 0.4 B (8/8) | 1.8 ± 0.5 AB (5/8) |
| PLGA-KAg + Chal. | 12.1 ± 2.3 A (9/9) | 1.0 ± 0.1 B (9/9) | 0.3 ± 0.1 A (5/9) | 0.8 ± 0.5 AC (2/9) | 4.7 ± 0.1 B (9/9) | 1.6 ± 0.5 AB (5/9) |

Lungs of vaccinated and virus challenged pigs were examined for gross lung lesions, microscopic lung lesions, immunohistochemistry (IHC) scores and viral titers in BAL fluid and nasal swab samples.
[a]Mean values of 7 or 9 pigs ± SEM are shown, in parentheses the number of positive/total number of pigs.
[b]Right apical, cardiac and diaphragmatic lobes were examined in each pigs and average score of 7 or 9 pigs under indicated pig group.
[c]Values have been transferred into log10 scale. Letters A, B and C represent groups of means under each parameter significantly different from each other ($P < 0.05$).
Means labeled with the same letter are not significantly different, while those with different letters are significantly different.
Data were analyzed by one way ANOVA followed by Tukey's post-hoc test.

What is claimed is:

1. A composition, comprising an inactivated swine influenza A virus and a nanoparticle; wherein the nanoparticle is associated with the inactivated swine influenza A virus, further comprising an adjuvant.

2. The composition of claim 1, wherein the nanoparticle is immunogenic.

3. The composition of claim 1, wherein the nanoparticle is conjugated with the inactivated swine influenza A virus.

4. The composition of claim 1, wherein the nanoparticle is selected from the group consisting of chitosan, calcium phosphate, and lipids of various bacteria.

5. The composition of claim 1, wherein the inactivated swine influenza A virus is the H1N1, H1N2 or H3N2 strain of swine influenza A virus.

6. The composition of claim 1, wherein the inactivated swine influenza A virus is inactivated by UV light.

7. A vaccine comprising a composition of claim 1 in a pharmaceutically acceptable carrier.

8. A method of eliciting an immune response against swine influenza A virus in a pig comprising administering to the pig the vaccine of claim 7.

9. The method of claim 8, wherein the vaccine is administered intranasally.

10. The composition of claim 1, wherein the nanoparticle comprises poly(lactide co-glycolide) (PLGA).

11. The composition of claim 4, wherein the various bacteria can be *E. coli*, mycobacteria, leptospira and mixtures thereof.

12. The composition of claim 1, wherein the adjuvant comprises a *Mycobacterium* lysate.

13. The composition of claim 1, wherein the adjuvant comprises a *Mycobacterium smegmatis* whole cell lysate.

14. The composition of claim 1, wherein the adjuvant comprises a *Mycobacterium tuberculosis* whole cell lysate.

15. The vaccine of claim 7, wherein the vaccine is administered at a dose of between 50 µg/pig and 1 mg/pig.

16. The vaccine of claim 15, wherein the vaccine is administered at a dose of between 100 µg/pig and 500 µg/pig.

17. The vaccine of claim 7, wherein the vaccine is administered as a single dose.

18. The vaccine of claim 7, where in the vaccine is administered in two or more doses.

19. The vaccine of claim 18, where in the two or more doses are administered at two-week intervals.

20. The vaccine of claim 7, wherein the vaccine is administered intranasally.

21. The vaccine of claim 7, wherein the composition contains between $1 \times 10^8$ and $1 \times 10^5$ $TCID_{50}$ of swine influenza A virus prior to inactivation.

22. A composition, comprising an inactivated swine influenza A virus and a nanoparticle; wherein the nanoparticle is associated with the inactivated swine influenza A virus, further comprising an adjuvant, wherein the composition contains between $1 \times 10^8$ and $1 \times 10^5$ $TCID_{50}$ of swine influenza A virus prior to inactivation.

* * * * *